United States Patent
Grammenos et al.

(10) Patent No.: US 9,055,750 B2
(45) Date of Patent: Jun. 16, 2015

(54) FUNGICIDAL PYRIMIDINE COMPOUNDS

(71) Applicants: Wassilios Grammenos, Ludwigshafen (DE); Ian Robert Craig, Ludwigshafen (DE); Nadege Boudet, Hemsbach (DE); Bernd Mueller, Frankenthal (DE); Jochen Dietz, Karlsruhe (DE); Erica May Wilson Lauterwasser, Mannheim (DE); Jan Klaas Lohmann, Lambsheim (DE); Jurith Montag, Ludwigshafen (DE)

(72) Inventors: Wassilios Grammenos, Ludwigshafen (DE); Ian Robert Craig, Ludwigshafen (DE); Nadege Boudet, Hemsbach (DE); Bernd Mueller, Frankenthal (DE); Jochen Dietz, Karlsruhe (DE); Erica May Wilson Lauterwasser, Mannheim (DE); Jan Klaas Lohmann, Lambsheim (DE); Jurith Montag, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/375,238

(22) PCT Filed: Feb. 1, 2013

(86) PCT No.: PCT/EP2013/052008
§ 371 (c)(1),
(2) Date: Jul. 29, 2014

(87) PCT Pub. No.: WO2013/113863
PCT Pub. Date: Aug. 8, 2013

(65) Prior Publication Data
US 2015/0024936 A1    Jan. 22, 2015

(30) Foreign Application Priority Data

Feb. 3, 2012   (EP) .................................... 12153760
Feb. 10, 2012  (EP) .................................... 12154879

(51) Int. Cl.
| | | |
|---|---|---|
| A01N 43/54 | (2006.01) |
| C07D 401/12 | (2006.01) |
| C07D 239/42 | (2006.01) |
| C07D 403/12 | (2006.01) |
| C07D 417/12 | (2006.01) |
| A61K 31/506 | (2006.01) |

(52) U.S. Cl.
CPC .............. *A01N 43/54* (2013.01); *A61K 31/506* (2013.01); *C07D 401/12* (2013.01); *C07D 239/42* (2013.01); *C07D 403/12* (2013.01); *C07D 417/12* (2013.01)

(58) Field of Classification Search
CPC ... C07D 401/12; C07D 403/12; A61K 31/506
See application file for complete search history.

(56) References Cited

U.S. PATENT DOCUMENTS 5,498,612 A * 3/1996 Obata et al. .................. 514/256
5,852,042 A   12/1998 Jakobi et al.

FOREIGN PATENT DOCUMENTS

| EP | 0 264 217 | 4/1988 |
|---|---|---|
| EP | 0 665 225 | 8/1995 |
| WO | WO 93/04580 | 3/1993 |
| WO | WO 94/04526 | 3/1994 |
| WO | WO 95/18795 | 7/1995 |
| WO | WO 96/10016 | 4/1996 |
| WO | WO 97/28133 | 8/1997 |
| WO | WO 9728133 A1 * | 8/1997 |
| WO | WO 98/03272 | 1/1998 |
| WO | WO 2007/046809 | 4/2007 |
| WO | WO 2010/025451 | 3/2010 |
| WO | WO 2011/025505 | 3/2011 |
| WO | WO 2011/085084 | 7/2011 |
| WO | WO 2013/113715 | 8/2013 |

OTHER PUBLICATIONS

European Search Report dated May 15, 2012, prepared in corresponding EP Application No. 12153760.
International Search Report, PCT/EP2013/052008, filed Feb. 1, 2013, report completed Mar. 11, 2013.
International Preliminary Report on Patentability, PCT/EP2013/052008, filed Feb. 1, 2013, report completed Feb. 5, 2014.

* cited by examiner

*Primary Examiner* — Alexander R Pagano
(74) *Attorney, Agent, or Firm* — Brinks Gilson & Lione

(57) ABSTRACT

The present invention relates to fungicidal pyrimidine compounds I, to their use and to methods for combating phytopathogenic fungi. The present invention also relates to seeds treated with at least one such compound. Furthermore the invention relates to processes for preparing compounds of formula I.

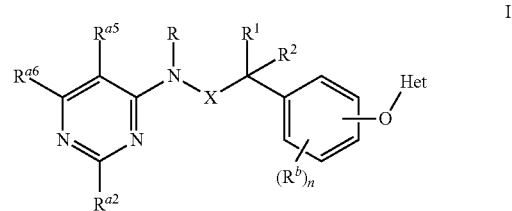

19 Claims, No Drawings

FUNGICIDAL PYRIMIDINE COMPOUNDS

This application is a National Stage application of International Application No. PCT/EP2013/052008, filed Feb. 1, 2013, the entire contents of which is hereby incorporated herein by reference. This application also claims priority under 35 U.S.C. §119 to European Patent Application No. 12153760.9, filed Feb. 3, 2012; and European Patent Application No. 12154879.6, filed Feb. 10, 2012; the entire contents of which are hereby incorporated herein by reference.

The present invention relates to fungicidal pyrimidine compounds, to their use and to methods for combating phytopathogenic fungi. The present invention also relates to seeds treated with at least one such compound. Furthermore the invention relates to processes for preparing compounds of formula I.

WO 98/03272 A1 describes a process for the preparation of 4-amino-5-chloro-6-(1-fluoroethyl)pyrimidine compounds, which are pest controlling agents for agricultural and horticultural use. WO 97/28133 A1 discloses acylated 4-amino and 4-hydrazinopyrimidines and their use as pesticides. WO 95/18795 A1 relates to N-(4-pyrimidinyl)amide pesticides and EP 665225 A1 relates to 4-phenethylamino pyrimidine derivatives useful for chemical control of noxious organisms.

The compounds according to the present invention differ from those described in the abovementioned publications in that the pyrimidine ring carries a halogen substituent in 6-position and/or the specific linker X as defined herein.

EP 264217 A2 generally discloses certain aryl alkyl amino pyrimidine derivatives inter alia with fungicidal activity of formula:

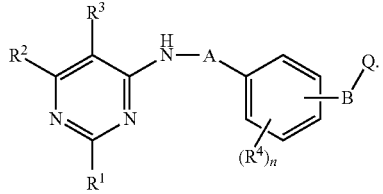

EP 264217 A2 does not mention the specific combination of a halogen substituent in 6-position of the pyrimidine ring and the specific ethylene linker unit —X—$CR^1R^2$ as defined herein together with a heteroaryloxy substitution of the phenyl ring.

In many cases, in particular at low application rates, the fungicidal activity of known fungicidal compounds is unsatisfactory. Based on this, it was an object of the present invention to provide compounds having improved activity and/or a broader activity spectrum against phytopathogenic fungi. This objective is achieved by the use of substituted pyrimidine compounds of formula I having good fungicidal activity against phytopathogenic harmful fungi.

Accordingly, the present invention relates to compounds of the formula I

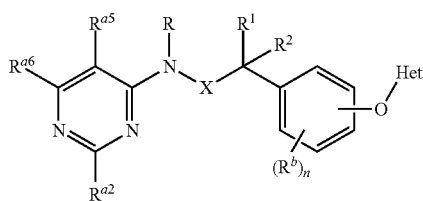

wherein:
$R^{a2}$, $R^{a5}$ independently of each other, are hydrogen, halogen, CN, $NO_2$, OH, SH, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_1$-$C_4$-alkoxy-$C_1$-$C_4$-alkyl, $C_1$-$C_4$-alkoxy-$C_1$-$C_4$-alkoxy, $C_2$-$C_4$-alkenyl, $C_2$-$C_4$-alkynyl, $C_2$-$C_4$-haloalkenyl, $C_2$-$C_4$-haloalkynyl, $C_3$-$C_8$-cycloalkyl, $C_3$-$C_8$-cycloalkyloxy, $C_3$-$C_8$-cycloalkyl-$C_1$-$C_4$-alkyl, $NR^AR^B$, C(=O)R', C(=NOR'')R''' or —C(=NH)—O—R''';

$R^A$, $R^B$ independently of each other are hydrogen, $C_1$-$C_4$-alkyl, $C_2$-$C_4$-alkenyl, $C_2$-$C_4$-alkynyl, phenyl, benzyl, $C_3$-$C_8$-cycloalkyl, $C_3$-$C_8$-cycloalkenyl or —C(=O)—R';

R' is hydrogen, OH, $NH_2$, $C_1$-$C_4$-alkyl, $C_1$-$C_4$-haloalkyl, $C_2$-$C_4$-alkenyl, $C_2$-$C_4$-alkynyl, $C_1$-$C_4$-alkoxy, $C_1$-$C_4$-haloalkoxy, $C_1$-$C_4$-alkylamino or di($C_1$-$C_4$-alkyl)amino;

R'' is hydrogen, $C_1$-$C_4$-alkyl, $C_1$-$C_4$-haloalkyl, $C_2$-$C_4$-alkenyl, $C_2$-$C_4$-alkynyl or $C_1$-$C_4$-alkoxy-$C_1$-$C_4$-alkyl;

R''' is hydrogen or $C_1$-$C_4$-alkyl;

$R^{a6}$ is halogen;

R is hydrogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkoxy-$C_1$-$C_4$-alkyl, $C_1$-$C_4$-haloalkoxy-$C_1$-$C_4$-alkyl, $C_2$-$C_4$-alkenyl, $C_2$-$C_4$-haloalkenyl, $C_2$-$C_4$-alkynyl, $C_2$-$C_4$-haloalkynyl, CN, $CH_2CN$, $NR^AR^B$ or $CH_2$—O—C(=O)R';

$R^1$, $R^2$ independently of each other are hydrogen, halogen, CN, OH, $C_1$-$C_4$-alkyl, $C_1$-$C_4$-haloalkyl, $C_1$-$C_4$-alkoxy, $C_1$-$C_4$-haloalkoxy, $C_1$-$C_4$-alkoxy-$C_1$-$C_4$-alkyl, $C_1$-$C_4$-haloalkoxy-$C_1$-$C_4$-alkyl, $C_2$-$C_4$-alkenyl, $C_2$-$C_4$-haloalkenyl, $C_2$-$C_4$-alkynyl, $C_2$-$C_4$-haloalkynyl, $C_3$-$C_8$-cycloalkyl, $C_3$-$C_8$-cycloalkyl-$C_1$-$C_4$-alkyl, $C_3$-$C_8$-cycloalkyloxy, $NR^AR^B$, C(=O)R', C(=NOR'')R''', —C(=NH)—O—R''' or benzyl wherein the phenyl moiety of benzyl is unsubstituted or carries 1, 2, 3, 4, or 5 substituents selected from the group consisting of CN, halogen, $C_1$-$C_4$-alkyl, $C_1$-$C_4$-haloalkyl, $C_1$-$C_4$-alkoxy, $C_1$-$C_4$-haloalkoxy, ($C_1$-$C_4$-alkoxy)carbonyl and di($C_1$-$C_4$-alkyl)aminocarbonyl, or two radicals $R^1$ and $R^2$ that are bound to the same carbon atom form together with said carbon atom a saturated or partially unsaturated 3-, 4-, 5-, 6-, or 7-membered carbocycle or a saturated or partially unsaturated 3-, 4-, 5-, 6-, or 7-membered heterocycle, wherein the ring member atoms of the abovementioned heterocycle include beside carbon atoms 1, 2, 3 or 4 heteroatoms selected from the group of N, O and S, and wherein the abovementioned cycle is unsubstituted or carries 1, 2, 3 or 4 substituents selected from halogen, CN, OH, SH, $C_1$-$C_4$-alkyl, $C_1$-$C_4$-alkoxy or $C_1$-$C_4$-alkylthio; and one or two $CH_2$ groups of the abovementioned cycles may be respectively replaced by one or two C(=O) or C(=S) groups;

X is a divalent group selected from —$CR^3R^4$—, —C(=$NR^D$)— and —C(=$NOR^D$)—, wherein
$R^D$ is hydrogen or $C_1$-$C_4$-alkyl, and wherein
$R^3$ and $R^4$ independently of each other are hydrogen, CN, $C_1$-$C_4$-hydroxyalkyl, $C_1$-$C_4$-alkyl, $C_1$-$C_4$-haloalkyl, $C_1$-$C_4$-alkoxy, $C_1$-$C_4$-haloalkoxy, $C_1$-$C_4$-alkoxy-$C_1$-$C_4$-alkyl, $C_1$-$C_4$-haloalkoxy-$C_1$-$C_4$-alkyl, $C_2$-$C_4$-alkenyl, $C_2$-$C_4$-haloalkenyl, $C_2$-$C_4$-alkynyl, $C_2$-$C_4$-haloalkynyl, $C_3$-$C_8$-cycloalkyl, $C_3$-$C_8$-cycloalkyl-$C_1$-$C_4$-alkyl, $C_3$-$C_8$-cycloalkyloxy, $NR^AR^B$, C(=O)R', C(=NOR'')R''', —C(=NH)—O—R''' or benzyl wherein the phenyl moiety of benzyl is unsubstituted or carries 1, 2, 3, 4, or 5 substituents selected from the group consisting of CN, halogen, $C_1$-$C_4$-alkyl, $C_1$-$C_4$-haloalkyl, $C_1$-$C_4$-alkoxy, $C_1$-$C_4$-haloalkoxy, ($C_1$-$C_4$-alkoxy)carbonyl and di($C_1$-$C_4$-alkyl)aminocarbonyl, or two radicals $R^3$ and $R^4$ that are bound to the same carbon atom form together with said carbon atom a saturated or partially unsaturated 3-, 4-, 5-, 6-, or 7-membered carbocycle or a saturated or partially unsaturated 3-, 4-, 5-, 6-, or 7-membered heterocycle, wherein the ring member atoms of the abovementioned heterocycle include beside carbon atoms 1, 2, 3 or 4 heteroatoms selected from the group of N, O and S, and wherein the abovementioned cycle is unsubstituted or carries 1, 2, 3 or 4 substituents selected from halogen, CN, OH, SH, $C_1$-$C_4$-alkyl, $C_1$-$C_4$-alkoxy or $C_1$-$C_4$-alkylthio; and one or two $CH_2$ groups of the abovementioned cycles may be respectively replaced by one or two C(=O) or C(=S) groups;

n indicates the number of substituents $R^b$ on the phenyl ring and n is 0, 1, 2, 3 or 4;

$R^b$ is halogen, CN, $NO_2$, $C_1$-$C_4$-alkyl, $C_1$-$C_4$-haloalkyl, $C_1$-$C_4$-alkoxy, $C_1$-$C_4$-haloalkoxy, $C_2$-$C_4$-alkenyl, $C_2$-$C_4$-haloalkenyl, $C_2$-$C_4$-alkynyl, $C_2$-$C_4$-haloalkynyl, $NR^A R^B$, C(=NOR")R''' or —C(=NH)—O—R''', it being possible for n=2, 3 or 4 that $R^b$ are identical or different;

Het is a 5- or 6-membered heteroaryl, wherein the ring member atoms of the heteroaryl include besides carbon atoms 1, 2, 3 or 4 heteroatoms selected from the group of N, O and S and wherein the heteroaryl is unsubstituted or carries 1, 2, 3 or 4 identical or different groups $R^c$:

$R^c$ is halogen, CN, $NO_2$, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylamino, di($C_1$-$C_6$-alkyl)amino, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_1$-$C_6$-alkoxy-$C_1$-$C_4$-alkyl, $C_1$-$C_6$-haloalkoxy-$C_1$-$C_4$-alkyl, $C_2$-$C_6$-alkenyl, $C_2$-$C_6$-alkynyl, C(=O)R', C(=NOR")R''', $C_3$-$C_8$-cycloalkyl, $C_3$-$C_8$-cycloalkyl-$C_1$-$C_4$-alkyl, phenyl, phenoxy, phenoxy-$C_1$-$C_4$-alkyl or a 5- or 6-membered heteroaryl, wherein the ring member atoms of the heteroaryl include besides carbon atoms 1, 2, 3 or 4 heteroatoms selected from the group of N, O and S, and wherein the aforementioned cyclic radicals are unsubstituted or carry 1, 2, 3 or 4 identical or different substituents $R^d$:

$R^d$ is halogen, CN, $C_1$-$C_4$-haloalkyl, $C_1$-$C_4$-alkoxy or $C_1$-$C_4$-haloalkoxy;

or two radicals $R^c$ that are bound to adjacent ring member atoms of the Het group form together with said ring member atoms a fused 5-, 6- or 7-membered saturated, partially unsaturated or aromatic carbocycle or heterocycle, wherein the ring member atoms of the fused heterocycle include besides carbon atoms 1, 2, 3 or 4 heteroatoms selected from the group of N, O and S, and wherein the fused carbocycle or heterocycle is unsubstituted or carries 1, 2, 3 or 4 identical or different radicals groups $R^e$:

$R^e$ is halogen, CN, $C_1$-$C_4$-haloalkyl, $C_1$-$C_4$-alkoxy or $C_1$-$C_4$-haloalkoxy;

and the N-oxides and the agriculturally acceptable salts of the compounds of formula I.

The present invention furthermore relates to processes for preparing compounds of formula I. Accordingly a 4-halopyrimidine compound II, wherein Hal is halogen, preferably Cl or F, can be reacted with a suitable phenethyl amine compound III, wherein X is —$CR^3R^4$—, to obtain a compound I according to the present invention, wherein X is —$CR^3R^4$—, as shown in Scheme 1.

Scheme 1

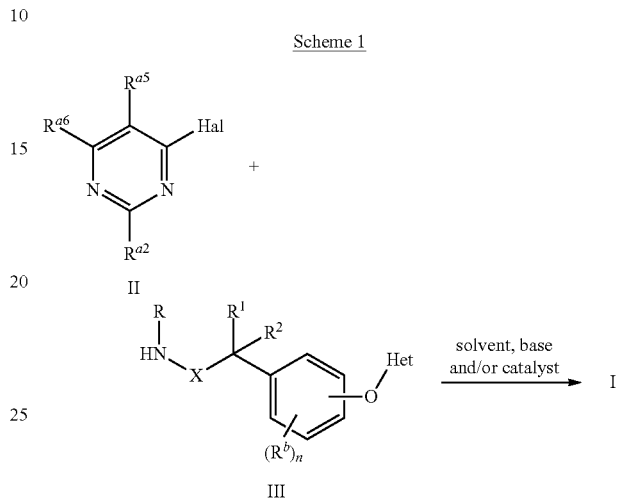

Generally, this reaction is carried out at temperatures of from 0 to 200° C., preferably from 50 to 170° C., in an inert organic solvent preferably in the presence of a base or a catalyst or a combination of a base and a catalyst (catalyst: e.g. NaF, KF, LiF, NaBr, KBr, LiBr, NaI, KI, LiI and ionic liquids, such as imidazolium catalysts).

Suitable solvents are aromatic hydrocarbons such as toluene, o-, m- and p-xylene; halogenated hydro-carbons such as chlorobenzene, dichlorobenzene; ethers such as dioxane, anisole and tetrahydrofuran (THF); nitriles such as acetonitrile and propionitrile; ketones, such as acetone, methyl ethyl ketone, diethyl ketone and tert.-butyl methyl ketone; alcohols such as ethanol, n-propanol, isopropanol, n-butanol and tert.-butanol; and also dimethyl sulfoxide (DMSO), dimethylformamide (DMF), dimethyl acetamide, N-methyl-2-pyrrolidone (NMP), N-ethyl-2-pyrrolidone (NEP) and acetic acid ethyl ester, preferably DMSO, DMF, dimethyl acetamide, NMP, or NEP. Particular preference is given to NMP. It is also possible to use mixtures of the solvents mentioned.

Suitable bases are, in general, inorganic compounds, such as alkali metal and alkaline earth metal hydroxides such as lithium hydroxide, sodium hydroxide, potassium hydroxide and calcium hydroxide; alkali metal and alkaline earth metal oxides such as lithium oxide, sodium oxide, potassium oxide and calcium oxide; alkali metal and alkaline earth metal phosphates such as lithium phosphate, sodium phosphate, potassium phosphate and calcium phosphate; alkali metal amides such as lithium amide, sodium amide and potassium amide; alkali metal and alkaline earth metal hydrides lithium hydride, sodium hydride, potassium hydride and calcium hydride; alkali metal and alkaline earth metal carbonates such as lithium carbonate, potassium carbonate and calcium carbonate, caesium carbonate; moreover organic bases, for example tertiary amines such as trimethyl-amine (TMA), triethylamine (TEA), tributylamine (TBA), diisopropylethylamine (DIPEA) and N-methyl-2-pyrrolidone (NMP), pyridine, substituted pyridines such as collidine, lutidine and 4 dimethylaminopyridine (DMAP), and also bicyclic amines. Preference is given to sodium hydride, potassium hydride, lithium carbonate, potassium carbonate, caesium carbonate, TEA, TBA and DIPEA, in particular DIPEA. The bases are generally employed in equimolar amounts, in excess or, if appropriate, as solvent. The amount of base is typically 1.1 to 5.0 molar equivalents relative to 1 mole of compounds II.

The starting materials are generally reacted with one another in equimolar amounts. In terms of yields, it may be advantageous to employ an excess of compounds III, based on 1.1 to 2.5 equivalents, preferred 1.1 to 1.5 equivalents of compounds II.

The compounds II are known from the literature or are commercially available or they can be prepared for example in analogy to methods described in: Heterocycles (2009) 78(7), 1627-1665; New J. Chem. (1994) 18(6), 701-8; WO 2005/095357; Science of Synthesis (2004) 16, 379-572; WO 2008/156726; WO 2006/072831; Organic Reactions (Hoboken, N.J., United States) (2000), 56; or Targets in Heterocyclic Systems (2008) 12, 59-84.

The phenethyl amine compounds III are known from the literature or are commercially available or they can be prepared for example in analogy to methods described in: WO 2007/046809; WO 2011/025505; or WO 2010/025451. Alternatively, compounds III in which $R^2$ is H and X is —$CR^3R^4$ can be prepared according to the general reaction in scheme 2:

Compound AD-1, in which the phenyl ring bears a hydroxyl group in ortho- or metha-position, is reacted with a heterocycle Het-LG, in which LG is a leaving group such as, e.g. F or Cl, in the presence of a base and/or a catalyst. Or compound AD-2, in which LG is a leaving group in para-position such as, e.g. F or Cl, is reacted with a hydroxyl-heterocycle HO-Het in the presence of a base and/or a catalyst according to procedures described in WO 2011032277 A1, WO 2008065393 A1, WO 2007096647 A2, WO 2007006714 A1, AU 2006201959 µl, DE 19518073 A1 (with catalyst: Organic Letters (2001), 3(26), 4315-4317; Journal of the American Chemical Society (1999), 121(18), 4369-4378) and provides Het-AD. Subsequent reaction with a nitroalkyl compound followed by a reduction leads to amine compounds III as described in Tetrahedron Letters (2003), 44(12), 2557-2560, Journal of Mass Spectrometry (2008), 43(4), 528-534, WO 2008039882 A1, Bioorganic & Medicinal Chemistry Letters (2007), 17(4), 974-977, Chemistry & Biodiversity (2005), 2(9), 1217-1231, Journal of Organic Chemistry (2005), 70(14), 5519-5527, Bioorganic & Medicinal Chemistry (2004), 12(15), 4055-4066 or Pesticide Science (1995), 44(4), 341-355.

Otherwise compounds III can be synthesized in analogy to WO 2011053835 A1, GB 2059955, WO 2007020227 A1, WO 2008046598 A1, WO 2011053835 A1, European Journal of Medicinal Chemistry (2009), 44(5), 2246-2251, Journal of Medicinal Chemistry (2007), 50(20), 5003-5011. Phenethylamines wherein $R^1$ and/or $R^2$ are not hydrogen are commercially available or can be prepared as outlined in scheme 3:

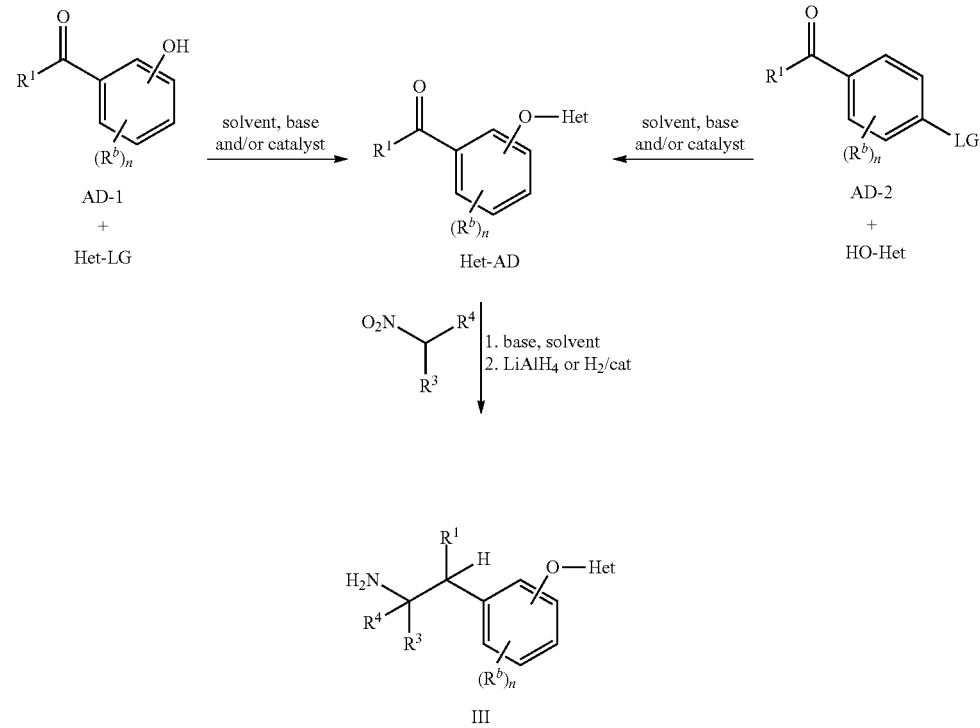

Scheme 2

Scheme 3

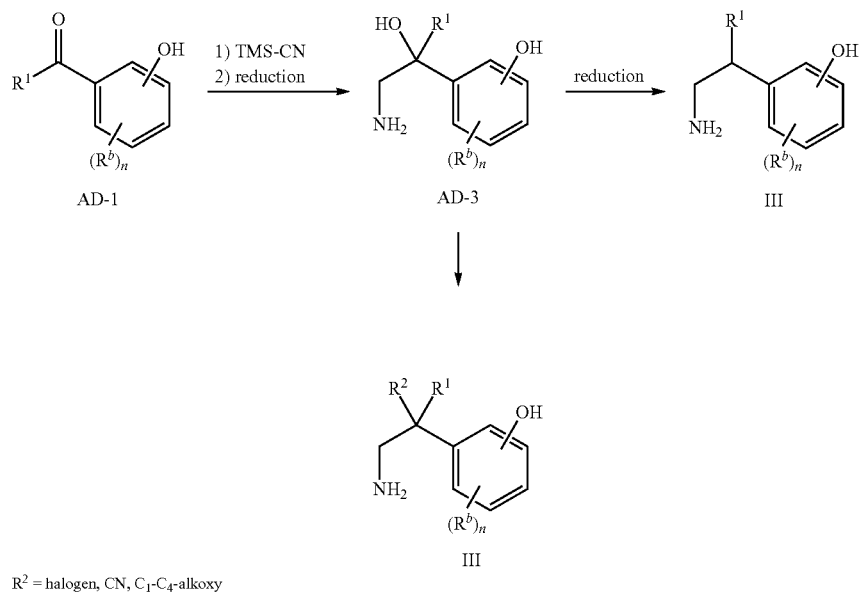

$R^2$ = halogen, CN, $C_1$-$C_4$-alkoxy

By addition of cyanide, a carbonyl compound AD-1 can be transformed into its cyano hyadrine (Chemistry A European Journal (2011), 17(44), 12276-12279; European Journal of Organic Chemistry (2002), (19), 3243-3249; Synlett (2003), (3), 353-356; Chirality (2009), 21(9), 836-842; Journal of Organic Chemistry (2008), 73(18), 7373-7375). Reduction of the nitrile group provides compounds AD-3 wherein $R^3$ and $R^4$ are hydrogen. Depending on the reaction conditions, the nitrile in AD-3 can be reduced and the hydroxyl group be removed in one step to furnish compounds III, wherein $R^3$ and $R^4$ are both hydrogen (Justus Liebigs Annalen der Chemie (1949), 564, 49-54, Justus Liebigs Annalen der Chemie (1957), 605, 200-11, Journal of the Chemical Society (1959), 1780-2, WO 2007020381 A2). Other conditions allow to preserve the hydroxyl group while selectively reducing the nitrile (Archiv der Pharmazie (Weinheim, Germany, 2011), 344(6), 372-385, Journal of the American Chemical Society (1948), 70, 3738-40, Journal of the American Chemical Society (1933), 55, 2593-7, Tetrahedron (2001), 57(40), 8573-8580, Chemical & Pharmaceutical Bulletin (2003), 51(6), 702-709;). This hydroxyl group can be transformed in a further step to provide halogen, cyano (Tetrahedron Letters (2007), 48(38), 6779-6784), amino, alkoxy groups by nucleophilic substitution in compounds such as III wherein $R^3$ and $R^4$ are hydrogen. It may be advantageous to couple AD-1 or AD-3 with a Het-LG prior to the abovementioned reactions as shown in scheme 2.

Phenethylamine compounds III, in which X is —$CR^3H$— can also be prepared by reductive amination of ketone compounds AD-4 as described in scheme 4.

Scheme 4

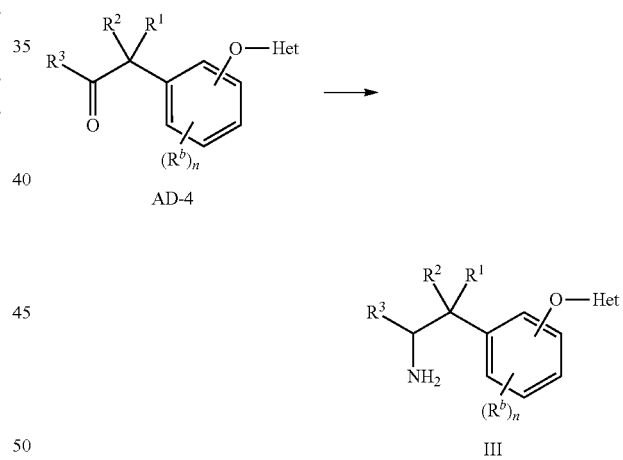

This conversion can be achieved using ammonia and a reducing agent or a metal organic compound or a cyanide source (Journal of the American Chemical Society (2011), 133(33), 12914-12917; Acta Pharmaceutica Suecica (1976), 13(1), 65-74; Journal of Medicinal Chemistry (1976), 19(6), 763-6; Journal of the American Chemical Society (1952), 74, 4611-15).

Phenethylamine compounds of the formula III, in which X is —$CR^3H$—, can also be prepared by transformation of AD-1 to a nitro alkene AD-6 by first reacting it with nitro alkyl compounds AD-5 preferably in the presence of a base as described in scheme 5 (Journal of Organic Chemistry, 67(14), 4875-4881; 2002; European Journal of Medicinal Chemistry, 46(9), 3986-3995; 2011; Journal of the American Chemical Society, 107(12), 3601-6; 1985).

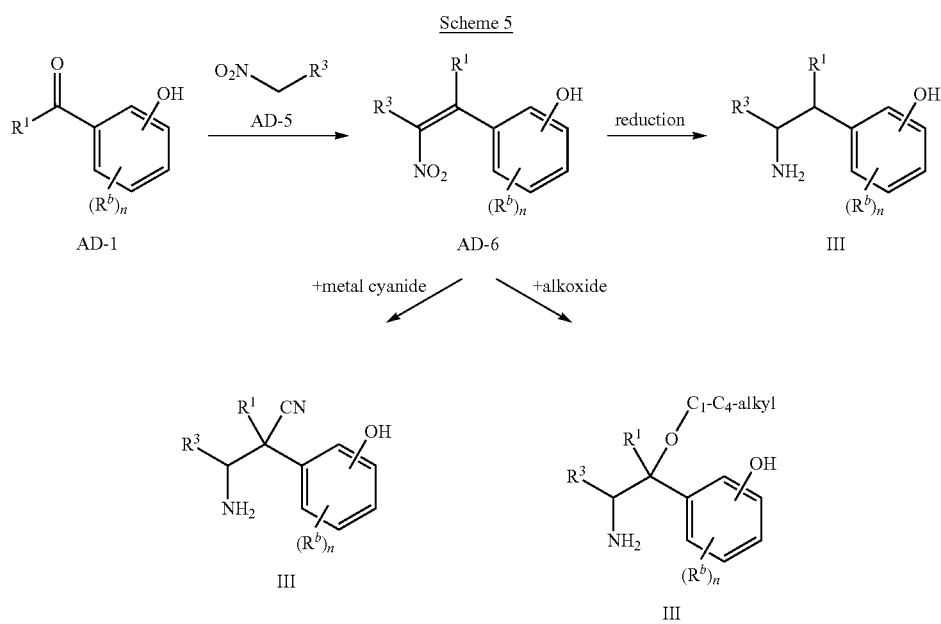

Consecutive reduction, e.g. with LiAlH$_4$ or hydrogen together with a suitable catalyst, leads to phenethylamine compounds III (Organic & Biomolecular Chemistry (2011), 9(23), 8171-8177, Journal of the American Chemical Society (2011), 133(31), 12197-12219, European Journal of Medicinal Chemistry (2010), 45(1), 11-18).

Alternatively, the nitro alkenes AD-6 can be reacted with an alkoxide to give the corresponding alkoxy compounds (European Journal of Medicinal Chemistry (2011), 46(9), 3986-3995, Organic Letters (2006), 8(20), 4481-4484, Tetrahedron (1999), 55(43), 12493-12514, Journal of Organic Chemistry (1995), 60(13), 4204-12)

Alternatively, the nitro alkenes can be reacted with metal cyanides to give the corresponding cyano compounds (Synlett (2008), (12), 1857-1861, Journal of Organic Chemistry (1985), 50(20), 3878-81). The terminal nitro group can be reduced selectively in the presence of the nitrile to yield compounds III, wherein R$^2$ is C$_1$-C$_4$-alkoxy or CN, respectively. It may be advantageous to couple AD-1 or AD-6 with a Het-LG prior to the abovementioned reactions as shown in scheme 2.

Alternatively, compounds of the formula III, in which X is —CH$_2$— can also be prepared by a process as described in scheme 6:

Scheme 6

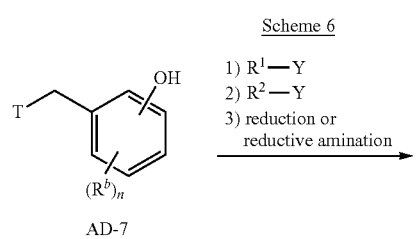

1) R$^1$—Y
2) R$^2$—Y
3) reduction or reductive amination

-continued

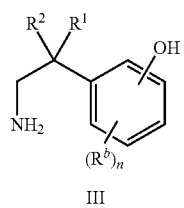

T = CHO or CN

Substituted benzyl nitrile or phenyl acetaldehyde compounds AD-7 can be alkylated (Tetrahedron (1988), 44(15), 4737-46; US 20080171761 A1, Jingxi Huagong Zhongjianti (2010), 40(3), 26-28, Advanced Synthesis & Catalysis (2011), 353(2+3), 501-507) once or twice using alkylation agents which carry a suitable leaving group Y and can then be transformed to the corresponding amine by reduction of the nitrile or imine intermediate respectively (WO 2010081692 A1, Tetrahedron Letters (1985), 26(36), 4299-300; Journal of Organic Chemistry (1981), 46(4), 783-8; Tetrahedron (2002), 58(8), 1513-1518). It may be advantageous to couple AD-7 with a Het-LG prior to the abovementioned reactions as shown in scheme 2.

Furthermore, substituted benzyl nitriles AD-9, which are available from benzyl halides AD-8, can be used as intermediates for the preparation of phenethylamines III, wherein R$^3$ and R$^4$ are hydrogen, according to scheme 7 by way of reduction with an appropriate reducing agent (e.g. LiAlH$_4$, PhSiH$_3$ or H$_2$ and a catalyst: Tetrahedron (2011), 67(42), 8183-8186, WO 2011088181 A1, European Journal of Inorganic Chemistry (2011), 2011(22), 3381-3386, WO 2008124757 A1).

Scheme 7

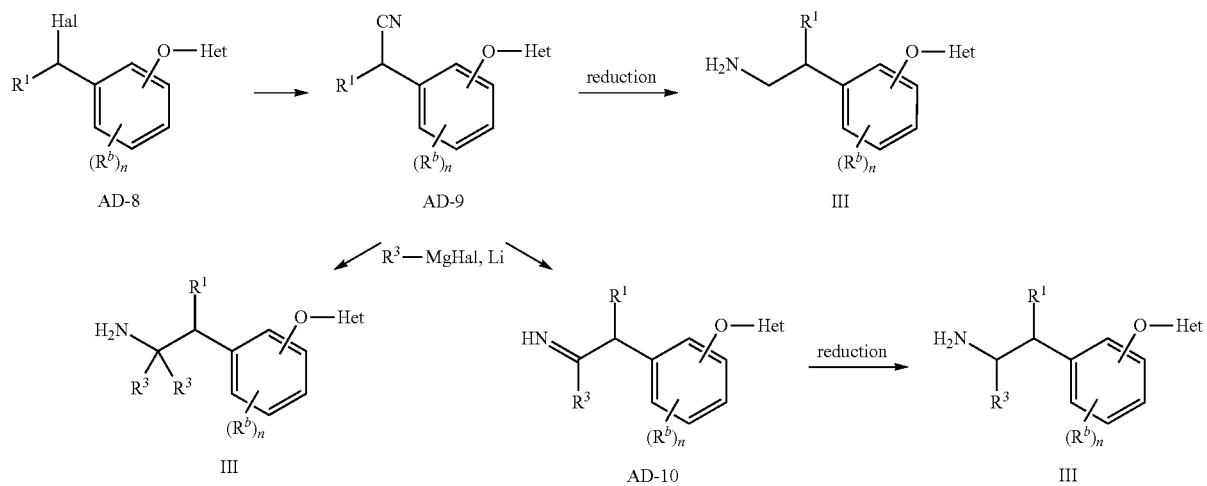

Further, compounds AD-9 can be used to obtain compounds III wherein at least one group $R^3$ or $R^4$ are not hydrogen. It is well known that benzyl nitriles such as AD-9 can undergo a selective addition of alkyl metals such as, for example, Grignard reagents $R^3MgHal$, in which Hal stands for chlorine, bromine or iodine, either furnishing compounds III wherein $R^3$ is not hydrogen and $R^4$ is hydrogen by reduction of an intermediate imine AD-10 with an appropriate reducing agent such as $NaBH_4$, Bioorganic & Medicinal Chemistry Letters (2011), 21(5), 1434-1437, WO 2010136493 A1, WO 2008034142 A2, Synthesis (1986), (4), 301-3), or, in case an excess of alkyl metal is employed, to directly obtain compounds III, wherein $R^3$ and $R^4$ are identical and both are, for example, $C_1$-$C_4$-alkyl (Organic Process Research & Development (2011), 15(4), 871-875, Journal of Medicinal Chemistry (1999), 42(19), 3965-3970, WO 2009156100 A1).

Compounds III can also be synthesized by way of hydroboration of substituted alkenes AD-12 (scheme 8) followed by Suzuki coupling using palladium catalysis (Journal of Organic Chemistry (2007), 72(22), 8422-8426; Organic Letters (2007), 9(2), 203-206, Journal of the American Chemical Society (2005), 127(29), 10186-10187).

Scheme 8

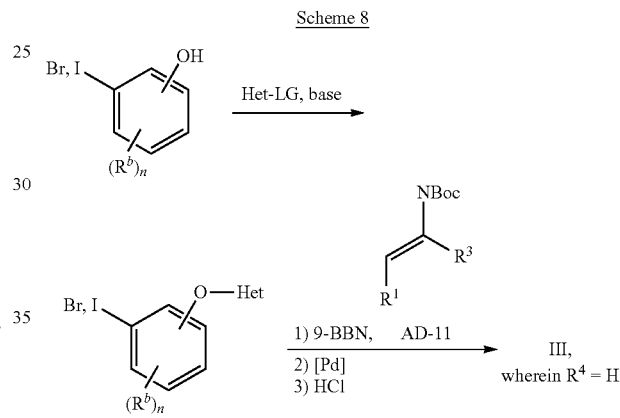

Compounds I in which X is —CH(C(=O)O—$C_1$-$C_4$-alkyl)-, —CH(C(=O)$NH_2$)—, —CH(C(=O)OH)— or —CHCN— can be prepared as follows or pursuing analogous procedures as in Scheme 9:

Scheme 9

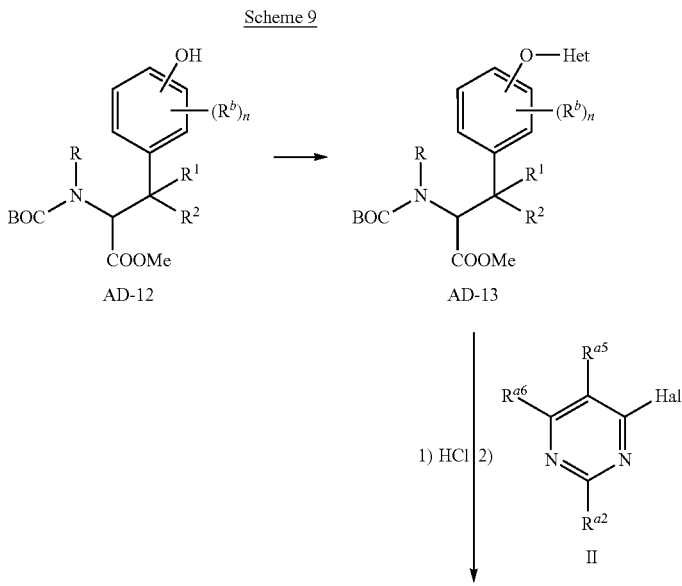

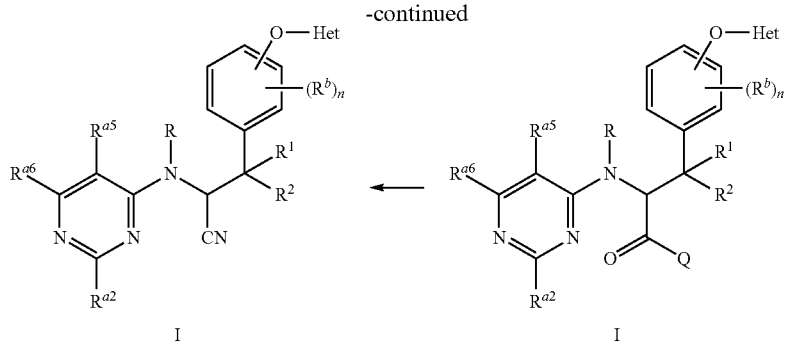

I

Tert-butyloxycarbonyl protected methyl ester AD-12 can be transformed to the corresponding biaryl ether AD-13 with suitable heteroaromatic groups Het-LG in analogy to WO 2005014534 A1, WO 2011100285 A1, Tetrahedron Letters (1994), 35(31), 5649-52. The coupling of AD-13 with 4-halopyrimidine compound II can be performed in analogy to Journal of Medicinal Chemistry (2011), 54(15), 5335-5348, Bioorganic & Medicinal Chemistry Letters (2011), 21(6), 1741-1743, US 20100068197 A1, WO 2005000246 A2, which leads to the formation of compounds I with Q being $C_1$-$C_4$-alkoxy (X is —CH(C(=O)—$C_1$-$C_4$-alkoxy)-). Saponificaton of the ester group with hydroxide bases leads to acid compounds I wherein X is —CH(C(=O)OH)—. Aminolysis of the ester group with ammonia and a catalyst (e.g. potassium cyanide) yields compounds I wherein X is —CH(C(=O)NH$_2$)—. Dehydratisation of the amide using POCl3 or trifluoro acetic acid anhydride with pyridine or treatment with other reagents capable to dehydrate a carboxamide such as, e.g., Burgess's reagent, leads to compound I, in which X is —CHCN— as described in WO 2006098961 A2.

A 4-halopyrimidine compound II, wherein Hal is halogen, preferably Cl or F, can be reacted with a suitable phenyl acetic acid amide compound III, wherein X is —C(=O)— to obtain a compound IVa

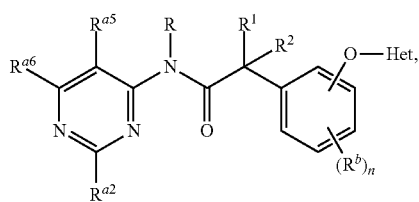

IVa in analogy to scheme 1.

Generally, this reaction is carried out at temperatures of from 0 to 200° C., preferably from 50 to 170° C., in an inert organic solvent preferably in the presence of a base or a catalyst or a combination of a base and a catalyst in a solvent.

Suitable catalysts are e.g. halides such as NaF, KF, LiF, NaBr, KBr, LiBr, NaI, KI, LiI; ionic liquids, such as imidazolium catalysts; transition metal catalysts like palladium, rhodium, ruthenium, iron, copper in the form of halides, pseudohalides, alkoxides, carboxylates (preferred acetate), complexes with dibenzylidene acetone and ligands like phosphine, phosphites, phosphoramidate ligands. Preferred ligands are bidentate and sterically demanding phosphorous ligands, even more preferably the catalysts are selected from 2,2'-bis(diphenyl-phosphanyl)-1,1'-binaphthyl, 2,2'-bis(diphenylphosphino)-1,1'-biphenyl, biphenyl-2-yldicyclohexylphosphine, 2-(dicyclohexylphosphino)-2',6'-dimethoxy-1,1'-biphenyl, 1,1-bis(diphenylphosphino)ferrocene, 9,9-dimethyl-4,5-bis(diphenylphosphino)xanthene, 1,2-bis(diphenylphosphino)ethane (dppe), 1,3-propanediylbis[diphenylphosphine], 1,4-butanediylbis[diphenylphosphine] and 1,1'-(1,2-ethanediyl)bis[1-(2-methoxyphenyl)-1-phenyl-diposphine.

Suitable solvents are aromatic hydrocarbons such as toluene, o-, m- and p-xylene; halogenated hydrocarbons such as chlorobenzene, dichlorobenzene; ethers such as dioxane, anisole and THF; nitriles such as acetonitrile and propionitrile; ketones such as acetone, methyl ethyl ketone, diethyl ketone and tert.-butyl methyl ketone; alcohols such as ethanol, n-propanol, isopropanol, n-butanol and tert.-butanol; and also DMSO, DMF, dimethyl acetamide, NMP, NEP and acetic acid ethyl ester. Preferably THF, DMSO, DMF, dimethyl acetamide, NMP or NEP are used; even more preferably THF, DMF or NMP are used. It is also possible to use mixtures of the solvents mentioned.

Suitable bases and their amounts are as described for the reaction with a phenethyl amine compound III, wherein X is —$CR^3R^4$—, as described above. The starting materials are generally reacted with one another in equimolar amounts. In terms of yields, it may be advantageous to employ an excess of compounds III, based on 1.1 to 2.5 equivalents, preferred 1.1 to 1.5 equivalents of compounds II.

The phenyl acetic acid amide compounds IIIa are known from the literature or are commercially available or they can be prepared for example in analogy to methods described in Organometallics (2011), 30(20), 5442-5451, WO 2010058030 A1 20100527, Journal of Organic Chemistry (1987), 52(21), 4689-93; GB 2016466 A.

Alternatively, amide compounds IVa can be synthesized by reacting 4-amino-pyrimidine compounds IIa [available by reaction of a chloropyrimidine II with excess of ammonia in analogy to methods described in WO 2011/147066, WO 2006/135719, US 2005/0245530 A1, J. Chem. Soc. (1951), 3439-44; Helv. Chim. Act. (1951), 34, 835-40] with the corresponding phenyl acetic acids IIIa in which Z is hydrogen or $C_1$-$C_4$-alkyl, which are commercially available, preferably in presence of AlMe$_3$ (1 to 3 equivalents) as stoichiometric reagent preferably in an inert organic solvent such as toluene (in analogy to US 2010/0063063 A1; WO 2005/011601; WO 2006/074884) as outlined in Scheme 10.

Scheme 10

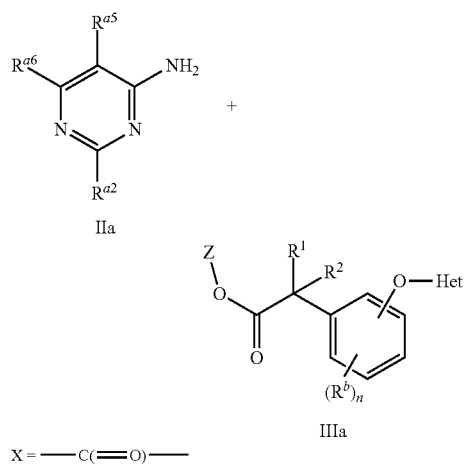

X = —C(=O)—

Compounds IVb can be prepared for example in analogy to methods described in US 20100022538 A1, J. Med. Chem. (2011), 54(9), 3241-3250, J. Org. Chem. (2011), 76(6), 1546-1553, Org. Lett. (2010), 12(23), 5570-5572.

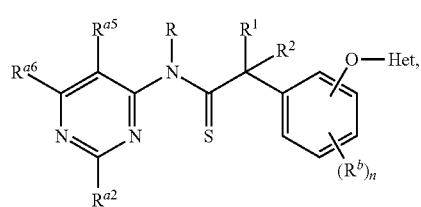

Compounds I, wherein X is —C(=NR$^D$)—, can be prepared from compounds IVa in analogy to Bioorg. Med. Chem. (2008) 16(8), 4600-4616, J. Med. Chem. (2004) 47(3), 663-672, Eur. J. Org. Chem. (2004) 5, 1025-1032, J. Med. Chem. (1987) 30(4), 720-1.

Compounds I, wherein X is —C(=NOR$^D$)—, can be prepared from compounds IVa in analogy to WO 2007/075598 or from compounds IVb according to WO 2008/039520 and O'zbekiston Kimyo Jurnali (2004) 4, 3-6.

Compounds I and intermediates, wherein R is hydrogen, can be converted by conventional processes such as alkylation. Examples of suitable alkylating agents include alkyl halides, such as alkyl chloride, alkyl bromide or alkyl iodide, examples being methyl chloride, methyl bromide or methyl iodide, or dialkyl sulfates such as dimethyl sulfate or diethyl sulfate. The reaction with the alkylating agent is carried out advantageously in the presence of a solvent. Solvents used for these reactions are—depending on temperature range—aliphatic, cycloaliphatic or aromatic hydrocarbons such as hexane, cyclohexane, toluene, xylene, chlorinated aliphatic and aromatic hydrocarbons such as DCM, chlorobenzene, open-chain dialkyl ethers such as diethyl ether, di-n-propyl ether, MTBE, cyclic ethers such as THF, 1,4-dioxane, glycol ethers such as dimethyl glycol ether, and also DMSO, DMF, dimethyl acetamide, NMP, NEP and acetic acid ethyl ester, preferably DMF, DMSO, NMP or NEP, or mixtures of these solvents.

If individual compounds I cannot be obtained by the routes described above, they can be prepared by derivatization of other compounds I. The N-oxides may be prepared from the compounds I according to conventional oxidation methods, e.g. by treating compounds I with an organic peracid such as metachloroperbenzoic acid (cf. WO 03/64572 or J. Med. Chem. (1995), 38(11), 1892-1903,); or with inorganic oxidizing agents such as hydrogen peroxide (cf. J. Heterocyc. Chem. (1981), 18 (7), 1305-1308) or oxone (cf. J. Am. Chem. Soc. (2001), 123 (25), 5962-5973). The oxidation may lead to pure mono-N-oxides or to a mixture of different N-oxides, which can be separated by conventional methods such as chromatography.

If the synthesis yields mixtures of isomers, a separation is generally not necessarily required since in some cases the individual isomers can be interconverted during work-up for use or during application (e.g. under the action of light, acids or bases). Such conversions may also take place after use, e.g. in the treatment of plants in the treated plant, or in the harmful fungus to be controlled.

The reaction mixtures are worked up in a customary manner, for example by mixing with water, separating the phases and, if appropriate, chromatic purification of the crude products. In some cases, the intermediates and end products are obtained in the form of colorless or slightly viscous oils which can be freed from volatile components or purified under reduced pressure and at moderately elevated temperatures. If the intermediates and end products are obtained as solids, purification can also be carried out by recrystallization or digestion.

The compounds of the present invention are useful for combating harmful fungi. Therefore the present invention furthermore relates to a method for combating harmful fungi, which process comprises treating the fungi or the materials, plants, the soil or seeds to be protected against fungal attack, with an effective amount of at least one compound of formula I or of an N-oxide or an agriculturally acceptable salt thereof.

Furthermore, the present invention also relates to seed comprising a compound of formula I, or an N-oxide or an agriculturally acceptable salt thereof, in an amount of from 0.1 g to 10 kg per 100 kg of seed.

Depending on the substitution pattern, the compounds of formula I and their N-oxides may have one or more centers of chirality, in which case they are present as pure enantiomers or pure diastereomers or as enantiomer or diastereomer mixtures. Both, the pure enantiomers or diastereomers and their mixtures are subject matter of the present invention.

Agriculturally useful salts of the compounds I encompass especially the salts of those cations or the acid addition salts of those acids whose cations and anions, respectively, have no adverse effect on the fungicidal action of the compounds I. Suitable cations are thus in particular the ions of the alkali metals, preferably sodium and potassium, of the alkaline earth metals, preferably calcium, magnesium and barium, of the transition metals, preferably manganese, copper, zinc and iron, and also the ammonium ion which, if desired, may carry one to four $C_1$-$C_4$-alkyl substituents and/or one phenyl or benzyl substituent, preferably diisopropylammonium, tetramethylammonium, tetrabutylammonium, trimethylbenzylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, propionate and butyrate. They can be formed by reacting a compound I with an acid of the corresponding anion, preferably of hydrochloric acid, hydrobromic acid, sulfuric acid, phosphoric acid or nitric acid.

Compounds I can be present in different crystal modifications whose biological activity may differ. They also form part of the subject matter of the present invention. The compounds of formula I can be present in atropisomers arising from restricted rotation about a single bond of asymmetric groups. They also form part of the subject matter of the present invention.

In respect of the variables, the embodiments of the intermediates correspond to the embodiments of the compounds of formula I. The term "compounds I" refers to compounds of formula I. Likewise, the term "compounds IIa" refers to compounds of formula IIa.

In the definitions of the variables given above, collective terms are used which are generally representative for the substituents in question. The term "$C_n$-$C_m$" indicates the number of carbon atoms possible in each case in the substituent or substituent moiety in question.

The term "halogen" refers to fluorine, chlorine, bromine and iodine.

The term "$C_1$-$C_4$-alkyl" refers to a straight-chained or branched saturated hydrocarbon group having 1 to 4 carbon atoms, for example methyl, ethyl, propyl, 1-methylethyl, butyl, 1-methylpropyl, 2-methylpropyl, and 1,1-dimethylethyl. Likewise, the term "$C_1$-$C_6$-alkyl" refers to a straight-chained or branched saturated hydrocarbon group having 1 to 6 carbon atoms.

The term "$C_1$-$C_4$-haloalkyl" refers to a straight-chained or branched alkyl group having 1 to 4 carbon atoms (as defined above), wherein some or all of the hydrogen atoms in these groups may be replaced by halogen atoms as mentioned above, for example chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, $CH_2$—$C_2F_5$, $CF_2$—$C_2F_5$, $CF(CF_3)_2$, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl. Likewise, the term "$C_1$-$C_6$-haloalkyl" refers to a straight-chained or branched alkyl group having 1 to 6 carbon atoms.

The term "$C_1$-$C_4$-alkoxy" refers to a straight-chain or branched alkyl group having 1 to 4 carbon atoms (as defined above) which is bonded via an oxygen, at any position in the alkyl group, for example methoxy, ethoxy, n-propoxy, 1-methylethoxy, butoxy, 1-methyl¬ propoxy, 2-methylpropoxy or 1,1-dimethylethoxy. Likewise, the term "$C_1$-$C_6$-alkoxy" refers to a straight-chain or branched alkyl group having 1 to 6 carbon atoms.

The term "$C_1$-$C_4$-hydroxyalkyl" refers to a straight-chained or branched alkyl group having 2 to 4 carbon atoms (as defined above), wherein one hydrogen atom in these groups may be replaced by one hydroxy group, for example hydroxymethyl, 2-hydroxyethyl, 3-hydroxy-propyl, 4-hydroxy-butyl.

The term "$C_1$-$C_4$-haloalkoxy" refers to a $C_1$-$C_4$-alkoxy group as defined above, wherein some or all of the hydrogen atoms may be replaced by halogen atoms as mentioned above, for example, $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy, 1-($CH_2Br$)-2-bromo¬ ethoxy, 4-fluorobutoxy, 4-chlorobutoxy, 4-bromobutoxy or nonafluorobutoxy. Likewise, the term "$C_1$-$C_6$-haloalkoxy" refers to a $C_1$-$C_6$-alkoxy group as defined above, wherein some or all of the hydrogen atoms may be replaced by halogen atoms as mentioned above.

The term "$C_1$-$C_4$-alkoxy-$C_1$-$C_4$-alkyl" refers to alkyl having 1 to 4 carbon atoms (as defined above), wherein one hydrogen atom of the alkyl radical is replaced by a $C_1$-$C_4$-alkoxy group (as defined above). Likewise, the term "$C_1$-$C_6$-alkoxy-$C_1$-$C_4$-alkyl" refers to alkyl having 1 to 4 carbon atoms (as defined above), wherein one hydrogen atom of the alkyl radical is replaced by a $C_1$-$C_6$-alkoxy group (as defined above).

The term "$C_1$-$C_4$-haloalkoxy-$C_1$-$C_4$-alkyl" refers to alkyl having 1 to 4 carbon atoms (as defined above), wherein one hydrogen atom of the alkyl radical is replaced by a $C_1$-$C_4$-haloalkoxy group (as defined above). Likewise, the term "$C_1$-$C_6$-haloalkoxy-$C_1$-$C_4$-alkyl" refers to alkyl having 1 to 4 carbon atoms (as defined above), wherein one hydrogen atom of the alkyl radical is replaced by a $C_1$-$C_6$-alkoxy group (as defined above).

The term "$C_1$-$C_4$-alkylthio" as used herein refers to straight-chain or branched alkyl groups having 1 to 4 carbon atoms (as defined above) bonded via a sulfur atom, at any position in the alkyl group, for example methylthio, ethylthio, propylthio, isopropylthio, and n butylthio. Likewise, the term "$C_1$-$C_6$-alkylthio" as used herein refers to straight-chain or branched alkyl groups having 1 to 6 carbon atoms (as defined above) bonded via a sulfur atom. Accordingly, the terms "$C_1$-$C_4$-haloalkylthio" and "$C_1$-$C_6$-haloalkylthio" as used herein refer to straight-chain or branched haloalkyl groups having 1 to 4 or 1 to 6 carbon atoms (as defined above) bonded through a sulfur atom, at any position in the haloalkyl group.

The terms "$C_1$-$C_4$-alkylsulfinyl" or "$C_1$-$C_6$-alkylsulfinyl" refer to straight-chain or branched alkyl groups having 1 to 4 or 1 to 6 carbon atoms (as defined above) bonded through a —S(=O)— moiety, at any position in the alkyl group, for example methylsulfinyl and ethylsulfinyl, and the like. Accordingly, the terms "$C_1$-$C_4$-haloalkylsulfinyl" and "$C_1$-$C_6$-haloalkylsulfinyl", respectively, refer to straight-chain or branched haloalkyl groups having 1 to 4 and 1 to 6 carbon atoms (as defined above), respectively, bonded through a —S(=O)— moiety, at any position in the haloalkyl group.

The terms "$C_1$-$C_4$-alkylsulfonyl" and "$C_1$-$C_6$-alkylsulfonyl", respectively, refer to straight-chain or branched alkyl groups having 1 to 4 and 1 to 6 carbon atoms (as defined above), respectively, bonded through a —S(=O)$_2$— moiety, at any position in the alkyl group, for example methylsulfonyl. Accordingly, the terms "$C_1$-$C_4$-haloalkylsulfonyl" and "$C_1$-$C_6$-haloalkylsulfonyl", respectively, refer to straight-chain or branched haloalkyl groups having 1 to 4 and 1 to 6 carbon atoms (as defined above), respectively, bonded through a —S(=O)$_2$— moiety, at any position in the haloalkyl group.

The term "$C_1$-$C_4$-alkylamino" refers to an amino radical carrying one $C_1$-$C_4$-alkyl group (as defined above) as substituent, for example methylamino, ethylamino, propylamino, 1-methylethylamino, butylamino, 1-methylpropylamino, 2-methylpropylamino, 1,1-di-methylethylamino and the like. Likewise, the term "$C_1$-$C_6$-alkylamino" refers to an amino radical carrying one $C_1$-$C_6$-alkyl group (as defined above) as substituent.

The term "di($C_1$-$C_4$-alkyl)amino" refers to an amino radical carrying two identical or different $C_1$-$C_4$-alkyl groups (as defined above) as substituents, for example dimethylamino, diethylamino, di-n-propylamino, diisopropylamino, N-ethyl-N-methylamino, N-(n-propyl)-N-methylamino, N-(isopropyl)-N methylamino, N-(n-butyl)-N-methylamino, N-(n-pentyl)-N-methylamino, N-(2-butyl)-N methylamino, N-(isobutyl)-N-methylamino, and the like. Likewise, the term "di($C_1$-$C_6$-alkyl)amino" refers to an amino radical carrying two identical or different $C_1$-$C_6$-alkyl groups (as defined above) as substituents.

The term "($C_1$-$C_4$-alkoxy)carbonyl" refers to a $C_1$-$C_4$-alkoxy radical (as defined above) which is attached via a carbonyl group.

The term "di($C_1$-$C_4$-alkyl)aminocarbonyl" refers to a di($C_1$-$C_4$)alkylamino radical as defined above which is attached via a carbonyl group.

The term "phenoxy" and refers to a phenyl radical which is attached via an oxygen atom. Likewise, the term "phenoxy-$C_1$-$C_4$-alkyl" and refers to a phenoxy radical which is attached via a $C_1$-$C_4$-alkyl group (as defined above).

The term "$C_2$-$C_4$-alkenyl" refers to a straight-chain or branched unsaturated hydrocarbon radical having 2 to 4 carbon atoms and a double bond in any position, such as ethenyl, 1-propenyl, 2-propenyl (allyl), 1-methylethenyl, 1-butenyl, 2-butenyl, 3-butenyl, 1-methyl-1-propenyl, 2-methyl-1-propenyl, 1-methyl-2-propenyl, 2-methyl-2-propenyl. Likewise, the term "$C_2$-$C_6$-alkenyl" refers to a straight-chain or branched unsaturated hydrocarbon radical having 2 to 6 carbon atoms and a double bond in any position.

The term "$C_2$-$C_4$-alkynyl" refers to a straight-chain or branched unsaturated hydrocarbon radical having 2 to 4 carbon atoms and containing at least one triple bond, such as ethynyl, 1-propynyl, 2-propynyl, 1-butynyl, 2-butynyl, 3-butynyl, 1-methyl-2-propynyl. Likewise, the term "$C_2$-$C_6$-alkynyl" refers to a straight-chain or branched unsaturated hydrocarbon radical having 2 to 6 carbon atoms and at least one triple bond.

The term "$C_3$-$C_8$-cycloalkyl" refers to monocyclic saturated hydrocarbon radicals having 3 to 8 carbon ring members, such as cyclopropyl ($C_3H_5$), cyclobutyl, cyclopentyl, cyclohexyl, cycloheptyl or cyclooctyl.

The term "$C_3$-$C_8$-cycloalkyl-$C_1$-$C_4$-alkyl" refers to a cycloalkyl radical having 3 to 8 carbon atoms (as defined above), which is bonded via a $C_1$-$C_4$-alkyl group (as defined above).

The term "$C_3$-$C_8$-cycloalkyloxy" refers to a cycloalkyl radical having 3 to 8 carbon atoms (as defined above), which is bonded via an oxygen.

The term "saturated or partially unsaturated 3-, 4-5-, 6- or 7-membered carbocycle" is to be understood as meaning both saturated or partially unsaturated carbocycles having 3, 4, 5, 6 or 7 ring members. Examples include cyclopropyl, cyclopentyl, cyclopentenyl, cyclopentadienyl, cyclohexyl, cyclohexenyl, cyclohexadienyl, cycloheptyl, cycloheptenyl, cycloheptadienyl, and the like.

The term "saturated or partially unsaturated 3-, 4-, 5-, 6-, or 7-membered heterocycle, wherein the ring member atoms of the heterocycle include besides carbon atoms 1, 2, 3 or 4 heteroatoms selected from the group of N, O and S", is to be understood as meaning both saturated and partially unsaturated heterocycles, for example:

a 3- or 4-membered saturated heterocycle which contains 1 or 2 heteroatoms from the group consisting of N, O and S as ring members such as oxirane, aziridine, thiirane, oxetane, azetidine, thiethane, [1,2]dioxetane, [1,2]dithietane, [1,2]diazetidine; and a 5- or 6-membered saturated or partially unsaturated heterocycle which contains 1, 2 or 3 heteroatoms from the group consisting of N, O and S as ring members such as 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl and also the corresponding—ylidene radicals; and a 7-membered saturated or partially unsaturated heterocycle such as tetra- and hexahydroazepinyl, such as 2,3,4,5-tetrahydro[1H]azepin-1-,-2-,-3-,-4-,-5-,-6- or -7-yl, 3,4,5,6-tetrahydro[2H]azepin-2-,-3-,-4-,-5-,-6- or -7-yl, 2,3,4,7-tetrahydro[1H]azepin-1-,-2-,-3-,-4-,-5-,-6- or -7-yl, 2,3,6,7-tetrahydro[1H]azepin-1-,-2-,-3-,-4-,-5-,-6- or -7-yl, hexahydroazepin-1-,-2-,-3- or -4-yl, tetra- and hexahydrooxepinyl such as 2,3,4,5-tetrahydro[1H]oxepin-2-,-3-,-4-,-5-,-6- or -7-yl, 2,3,4,7-tetrahydro[1H]oxepin-2-,-3-,-4-,-5-,-6- or -7-yl, 2,3,6,7-tetrahydro[1H]oxepin-2-, -3-,-4-,-5-,-6- or -7-yl, hexahydroazepin-1-,-2-,-3- or -4-yl, tetra- and hexahydro-1,3-diazepinyl, tetra- and hexahydro-1,4-diazepinyl, tetra- and hexahydro-1,3-oxazepinyl, tetra- and hexahydro-1,4-oxazepinyl, tetra- and hexahydro-1,3-dioxepinyl, tetra- and hexahydro-1,4-dioxepinyl and the corresponding—ylidene radicals; and The term "5- or 6-membered heteroaryl, wherein the ring member atoms of the heteroaryl include besides carbon atoms 1, 2, 3 or 4 heteroatoms selected from the group of N, O and S", refers to, for example,

- a 5-membered heteroaryl such as pyrrol-1-yl, pyrrol-2-yl, pyrrol-3-yl, thien-2-yl, thien-3-yl, furan-2-yl, furan-3-yl, pyrazol-1-yl, pyrazol-3-yl, pyrazol-4-yl, pyrazol-5-yl, imidazol-1-yl, imidazol-2-yl, imidazol-4-yl, imidazol-5-yl, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1,2,4-triazolyl-1-yl, 1,2,4-triazol-3-yl 1,2,4-triazol-5-yl, 1,2,4-oxadiazol-3-yl, 1,2,4-oxadiazol-5-yl and 1,2,4-thiadiazol-3-yl, 1,2,4-thiadiazol-5-yl; or
- a 6-membered heteroaryl, such as pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl and 1,3,5-triazin-2-yl and 1,2,4-triazin-3-yl.

The term "two radicals $R^c$ that are bound to adjacent ring member atoms form together with said ring member atoms a fused cycle" refers to a condensed bicyclic ring system, wherein 5- or 6-membered heteroaryl carries a fused-on 5-, 6- or 7-membered carbocyclic or heterocyclic ring it being possible that these rings are saturated or partially saturated or aromatic.

The term "one or two $CH_2$ groups of the abovementioned cycles may be respectively replaced by one or two $C(=O)$ or $C(=S)$ groups" refers to an exchange of carbon atoms from a saturated or partially unsaturated 3-, 4-, 5-, 6- or 7-membered carbocycle or a saturated or partially unsaturated 3-, 4-, 5-, 6- or 7-membered heterocycle, resulting in cycles such as cyclopropanone, cyclopentanone, cyclopropanethione, cyclopentanethione, 5-oxazolone, cyclohexane-1,4-dione, cyclohexane-1,4-dithione, cyclohex-2-ene-1,4-dione or cyclohex-2-ene-1,4-dithione.

As regards the fungicidal activity of the compounds I, I.A, I.B or I.C preference is given to those compounds, wherein the substituents and variables (e.g. $R^{a2}$, $R^{a5}$, $R^{a6}$, R, X, $R^1$, $R^2$, $R^3$, $R^4$, $R^b$, $R^c$, R', R''', $R^A$, $R^B$, $R^D$, Het, n) have independently of each other or more preferably in combination the following meanings:

A further embodiment relates to compounds I wherein $R^{a2}$ and $R^{a5}$ independently of each other are preferably selected from the group consisting of hydrogen, halogen, CN, $C_1$-$C_4$-alkoxy, $C_1$-$C_4$-alkoxy-$C_1$-$C_4$-alkyl, $C_1$-$C_4$-alkoxy-$C_1$-$C_4$-alkoxy, $C_1$-$C_4$-haloalkoxy, $C_1$-$C_4$-alkylthio, $C_1$-$C_4$-haloalkylthio, $C_2$-$C_4$-alkenyl, $C_2$-$C_4$-alkynyl, $C_3$-$C_8$-cycloalkyl, $C_3$-$C_8$-cycloalkyloxy, ($C_1$-$C_4$-alkoxy)carbonyl. Further preferred embodiments relate to compounds I wherein $R^{a2}$ and $R^{a5}$ independently of each other are hydrogen, halogen, CN, $C_1$-$C_4$-alkyl, $C_1$-$C_4$-haloalkyl, $C_1$-$C_4$-alkoxy, $C_1$-$C_4$-haloalkoxy, $C_1$-$C_4$-alkoxy-$C_1$-$C_4$-alkyl, $C_1$-$C_4$-alkoxy-$C_1$-$C_4$-alkoxy and ($C_1$-$C_4$-alkoxy)carbonyl. Further preferred embodiments relate to compounds I wherein $R^{a2}$ and $R^{a5}$ independently of each other are halogen, CN, $C_1$-$C_4$-alkyl, $C_1$-$C_4$-haloalkyl, $C_1$-$C_4$-alkoxy, $C_1$-$C_4$-haloalk-oxy, $C_1$-$C_4$-alkoxy-$C_1$-$C_4$-alkoxy or ($C_1$-$C_4$-alkoxy)carbonyl, and it being possible that one of both, $R^{a2}$ or $R^{a5}$ can in addition be hydrogen. Further preferred embodiments relate to compounds I wherein $R^{a2}$ and $R^{a5}$ independently of each other are hydrogen, Cl, F, $CH_3$, $CH_2CH_3$, $OCH_3$, $OCF_3$, $CH_2OCH_3$, CN, $OCH_2OCH_3$, $CF_3$, $CHFCH_3$, $COOCH_3$ or $COOCH_2CH_3$.

Further preferred embodiments relate to compounds I wherein $R^{a5}$ is Cl.

Further preferred embodiments relate to compounds I wherein $R^{a5}$ is F.

Further preferred embodiments relate to compounds I wherein $R^{a5}$ is $CH_3$.

Further preferred embodiments relate to compounds I wherein $R^{a5}$ is $OCH_3$.

In the compounds I according to the invention, $R^A$, $R^B$ in radicals $R^{a2}$ and $R^{a5}$ independently of one another preferably are hydrogen, $C_1$-$C_4$-alkyl.

In the compounds I according to the invention, R' in radicals $R^{a2}$ and $R^{a5}$ preferably is hydrogen, $NH_2$, $C_1$-$C_4$-alkyl, $C_1$-$C_4$-alkoxy. In the compounds I according to the invention, R'' in radicals $R^{a2}$ and $R^{a5}$ preferably is hydrogen, $C_1$-$C_4$-alkyl. In the compounds I according to the invention, R''' in radicals $R^{a2}$ and $R^{a5}$ preferably is hydrogen.

Further preferred embodiments relate to compounds I wherein $R^{a2}$ and $R^{a5}$ in each case are one of the following combinations in line 1 to line 196 in table A:

TABLE A

| line | $R^{a2}$ | $R^{a5}$ |
|---|---|---|
| 1 | H | H |
| 2 | $CH_3$ | H |
| 3 | $CH_2CH_3$ | H |
| 4 | $OCH_3$ | H |
| 5 | $CH_2OCH_3$ | H |
| 6 | $OCH_2OCH_3$ | H |
| 7 | $CF_3$ | H |
| 8 | $CHFCH_3$ | H |
| 9 | CN | H |
| 10 | F | H |
| 11 | Cl | H |
| 12 | $COOCH_3$ | H |
| 13 | $COOCH_2CH_3$ | H |
| 14 | $OCF_3$ | H |
| 15 | H | $CH_3$ |
| 16 | $CH_3$ | $CH_3$ |
| 17 | $CH_2CH_3$ | $CH_3$ |
| 18 | $OCH_3$ | $CH_3$ |
| 19 | $CH_2OCH_3$ | $CH_3$ |
| 20 | $OCH_2OCH_3$ | $CH_3$ |
| 21 | $CF_3$ | $CH_3$ |
| 22 | $CHFCH_3$ | $CH_3$ |
| 23 | CN | $CH_3$ |
| 24 | F | $CH_3$ |
| 25 | Cl | $CH_3$ |
| 26 | $COOCH_3$ | $CH_3$ |
| 27 | $COOCH_2CH_3$ | $CH_3$ |
| 28 | $OCF_3$ | $CH_3$ |
| 29 | H | $CH_2CH_3$ |
| 30 | $CH_3$ | $CH_2CH_3$ |
| 31 | $CH_2CH_3$ | $CH_2CH_3$ |
| 32 | $OCH_3$ | $CH_2CH_3$ |
| 33 | $CH_2OCH_3$ | $CH_2CH_3$ |
| 34 | $OCH_2OCH_3$ | $CH_2CH_3$ |
| 35 | $CF_3$ | $CH_2CH_3$ |
| 36 | $CHFCH_3$ | $CH_2CH_3$ |
| 37 | CN | $CH_2CH_3$ |
| 38 | F | $CH_2CH_3$ |
| 39 | Cl | $CH_2CH_3$ |
| 40 | $COOCH_3$ | $CH_2CH_3$ |
| 41 | $COOCH_2CH_3$ | $CH_2CH_3$ |
| 42 | $OCF_3$ | $CH_2CH_3$ |
| 43 | H | $OCH_3$ |
| 44 | $CH_3$ | $OCH_3$ |
| 45 | $CH_2CH_3$ | $OCH_3$ |
| 46 | $OCH_3$ | $OCH_3$ |
| 47 | $CH_2OCH_3$ | $OCH_3$ |
| 48 | $OCH_2OCH_3$ | $OCH_3$ |
| 49 | $CF_3$ | $OCH_3$ |
| 50 | $CHFCH_3$ | $OCH_3$ |
| 51 | CN | $OCH_3$ |
| 52 | F | $OCH_3$ |
| 53 | Cl | $OCH_3$ |
| 54 | $COOCH_3$ | $OCH_3$ |

TABLE A-continued

| line | $R^{a2}$ | $R^{a5}$ |
|---|---|---|
| 55 | COOCH$_2$CH$_3$ | OCH$_3$ |
| 56 | OCF$_3$ | OCH$_3$ |
| 57 | H | CH$_2$OCH$_3$ |
| 58 | CH$_3$ | CH$_2$OCH$_3$ |
| 59 | CH$_2$CH$_3$ | CH$_2$OCH$_3$ |
| 60 | OCH$_3$ | CH$_2$OCH$_3$ |
| 61 | CH$_2$OCH$_3$ | CH$_2$OCH$_3$ |
| 62 | OCH$_2$OCH$_3$ | CH$_2$OCH$_3$ |
| 63 | CF$_3$ | CH$_2$OCH$_3$ |
| 64 | CHFCH$_3$ | CH$_2$OCH$_3$ |
| 65 | CN | CH$_2$OCH$_3$ |
| 66 | F | CH$_2$OCH$_3$ |
| 67 | Cl | CH$_2$OCH$_3$ |
| 68 | COOCH$_3$ | CH$_2$OCH$_3$ |
| 69 | COOCH$_2$CH$_3$ | CH$_2$OCH$_3$ |
| 70 | OCF$_3$ | CH$_2$OCH$_3$ |
| 71 | H | OCH$_2$OCH$_3$ |
| 72 | CH$_3$ | OCH$_2$OCH$_3$ |
| 73 | CH$_2$CH$_3$ | OCH$_2$OCH$_3$ |
| 74 | OCH$_3$ | OCH$_2$OCH$_3$ |
| 75 | CH$_2$OCH$_3$ | OCH$_2$OCH$_3$ |
| 76 | OCH$_2$OCH$_3$ | OCH$_2$OCH$_3$ |
| 77 | CF$_3$ | OCH$_2$OCH$_3$ |
| 78 | CHFCH$_3$ | OCH$_2$OCH$_3$ |
| 79 | CN | OCH$_2$OCH$_3$ |
| 80 | F | OCH$_2$OCH$_3$ |
| 81 | Cl | OCH$_2$OCH$_3$ |
| 82 | COOCH$_3$ | OCH$_2$OCH$_3$ |
| 83 | COOCH$_2$CH$_3$ | OCH$_2$OCH$_3$ |
| 84 | OCF$_3$ | OCH$_2$OCH$_3$ |
| 85 | H | CF$_3$ |
| 86 | CH$_3$ | CF$_3$ |
| 87 | CH$_2$CH$_3$ | CF$_3$ |
| 88 | OCH$_3$ | CF$_3$ |
| 89 | CH$_2$OCH$_3$ | CF$_3$ |
| 90 | OCH$_2$OCH$_3$ | CF$_3$ |
| 91 | CF$_3$ | CF$_3$ |
| 92 | CHFCH$_3$ | CF$_3$ |
| 93 | CN | CF$_3$ |
| 94 | F | CF$_3$ |
| 95 | Cl | CF$_3$ |
| 96 | COOCH$_3$ | CF$_3$ |
| 97 | COOCH$_2$CH$_3$ | CF$_3$ |
| 98 | OCF$_3$ | CF$_3$ |
| 99 | H | CHFCH$_3$ |
| 100 | CH$_3$ | CHFCH$_3$ |
| 101 | CH$_2$CH$_3$ | CHFCH$_3$ |
| 102 | OCH$_3$ | CHFCH$_3$ |
| 103 | CH$_2$OCH$_3$ | CHFCH$_3$ |
| 104 | OCH$_2$OCH$_3$ | CHFCH$_3$ |
| 105 | CF$_3$ | CHFCH$_3$ |
| 106 | CHFCH$_3$ | CHFCH$_3$ |
| 107 | CN | CHFCH$_3$ |
| 108 | F | CHFCH$_3$ |
| 109 | Cl | CHFCH$_3$ |
| 110 | COOCH$_3$ | CHFCH$_3$ |
| 111 | COOCH$_2$CH$_3$ | CHFCH$_3$ |
| 112 | OCF$_3$ | CHFCH$_3$ |
| 113 | H | CN |
| 114 | CH$_3$ | CN |
| 115 | CH$_2$CH$_3$ | CN |
| 116 | OCH$_3$ | CN |
| 117 | CH$_2$OCH$_3$ | CN |
| 118 | OCH$_2$OCH$_3$ | CN |
| 119 | CF$_3$ | CN |
| 120 | CHFCH$_3$ | CN |
| 121 | CN | CN |
| 122 | F | CN |
| 123 | Cl | CN |
| 124 | COOCH$_3$ | CN |
| 125 | COOCH$_2$CH$_3$ | CN |
| 126 | OCF$_3$ | CN |
| 127 | H | F |
| 128 | CH$_3$ | F |
| 129 | CH$_2$CH$_3$ | F |
| 130 | OCH$_3$ | F |
| 131 | CH$_2$OCH$_3$ | F |
| 132 | OCH$_2$OCH$_3$ | F |
| 133 | CF$_3$ | F |
| 134 | CHFCH$_3$ | F |
| 135 | CN | F |
| 136 | F | F |
| 137 | Cl | F |
| 138 | COOCH$_3$ | F |
| 139 | COOCH$_2$CH$_3$ | F |
| 140 | OCF$_3$ | F |
| 141 | H | Cl |
| 142 | CH$_3$ | Cl |
| 143 | CH$_2$CH$_3$ | Cl |
| 144 | OCH$_3$ | Cl |
| 145 | CH$_2$OCH$_3$ | Cl |
| 146 | OCH$_2$OCH$_3$ | Cl |
| 147 | CF$_3$ | Cl |
| 148 | CHFCH$_3$ | Cl |
| 149 | CN | Cl |
| 150 | F | Cl |
| 151 | Cl | Cl |
| 152 | COOCH$_3$ | Cl |
| 153 | COOCH$_2$CH$_3$ | Cl |
| 154 | OCF$_3$ | Cl |
| 155 | H | COOCH$_3$ |
| 156 | CH$_3$ | COOCH$_3$ |
| 157 | CH$_2$CH$_3$ | COOCH$_3$ |
| 158 | OCH$_3$ | COOCH$_3$ |
| 159 | CH$_2$OCH$_3$ | COOCH$_3$ |
| 160 | OCH$_2$OCH$_3$ | COOCH$_3$ |
| 161 | CF$_3$ | COOCH$_3$ |
| 162 | CHFCH$_3$ | COOCH$_3$ |
| 163 | CN | COOCH$_3$ |
| 164 | F | COOCH$_3$ |
| 165 | Cl | COOCH$_3$ |
| 166 | COOCH$_3$ | COOCH$_3$ |
| 167 | COOCH$_2$CH$_3$ | COOCH$_3$ |
| 168 | OCF$_3$ | COOCH$_3$ |
| 169 | H | COOCH$_2$CH$_3$ |
| 170 | CH$_3$ | COOCH$_2$CH$_3$ |
| 171 | CH$_2$CH$_3$ | COOCH$_2$CH$_3$ |
| 172 | OCH$_3$ | COOCH$_2$CH$_3$ |
| 173 | CH$_2$OCH$_3$ | COOCH$_2$CH$_3$ |
| 174 | OCH$_2$OCH$_3$ | COOCH$_2$CH$_3$ |
| 175 | CF$_3$ | COOCH$_2$CH$_3$ |
| 176 | CHFCH$_3$ | COOCH$_2$CH$_3$ |
| 177 | CN | COOCH$_2$CH$_3$ |
| 178 | F | COOCH$_2$CH$_3$ |
| 179 | Cl | COOCH$_2$CH$_3$ |
| 180 | COOCH$_3$ | COOCH$_2$CH$_3$ |
| 181 | COOCH$_2$CH$_3$ | COOCH$_2$CH$_3$ |
| 182 | OCF$_3$ | COOCH$_2$CH$_3$ |
| 183 | H | OCF$_3$ |
| 184 | CH$_3$ | OCF$_3$ |
| 185 | CH$_2$CH$_3$ | OCF$_3$ |
| 186 | OCH$_3$ | OCF$_3$ |
| 187 | CH$_2$OCH$_3$ | OCF$_3$ |
| 188 | OCH$_2$OCH$_3$ | OCF$_3$ |
| 189 | CF$_3$ | OCF$_3$ |
| 190 | CHFCH$_3$ | OCF$_3$ |
| 191 | CN | OCF$_3$ |
| 192 | F | OCF$_3$ |
| 193 | Cl | OCF$_3$ |
| 194 | COOCH$_3$ | OCF$_3$ |
| 195 | COOCH$_2$CH$_3$ | OCF$_3$ |
| 196 | OCF$_3$ | OCF$_3$ |

In the compounds I according to the invention, $R^{a6}$ preferably is chlorine.

In the compounds I according to the invention, $R^{a6}$ preferably is fluorine.

In the compounds I according to the invention, $R^{a6}$ preferably is bromine.

In the compounds I according to the invention, R is preferably selected from the group consisting of hydrogen, $C_1$-$C_4$-alkyl, $C_1$-$C_4$-alkoxy, $C_1$-$C_4$-alkoxy-$C_1$-$C_4$-alkyl, $C_2$-$C_4$-alkenyl, $C_2$-$C_4$-alkynyl, CN, CH$_2$CN or CH$_2$—O—C(=O)R', wherein R' is hydrogen, $C_1$-$C_4$-alkyl, $C_1$-$C_4$-alkoxy;

more preferably R is selected from the group consisting of hydrogen, $C_1$-$C_4$-alkyl, $C_1$-$C_4$-alkoxy-$C_1$-$C_4$-alkyl, $C_2$-$C_4$-alkenyl and $C_2$-$C_4$-alkynyl; most preferably R is hydrogen or $C_1$-$C_4$-alkyl.

Another particularly preferred embodiment relates to compounds I wherein R is hydrogen; yet another preferred embodiment relates to compounds I wherein R is $CH_3$. Further preferred embodiments relate to compounds I wherein R is in each case one of the following groups I-1 to I-2 in table I:

TABLE I

| No. | R |
|---|---|
| I-1 | H |
| I-2 | $CH_3$ |

In the compounds I according to the invention, X is preferably —$CH_2$—, —$CH(CH_3)$—, —$CH(CH_2CH_3)$—, —$C(CH_3)_2$—, —CHCN—, —$CH(C(=O)$—$C_1$-$C_4$-alkoxy)-, —$CH(C(=O)NH_2)$—, —$C(=O)N(C_1$-$C_4$-alkyl)$_2$- and —$CH(C(=O)OH)$—; more preferably X is —$CH_2$— or —$CH(CH_2OH)$—, in particular X is —$CH_2$—. Further preferred embodiments relate to compounds I wherein X is in each case one of the following groups II-1 to II-7 in table II:

TABLE II

| No. | X |
|---|---|
| II-1 | —$CH_2$— |
| II-2 | —$C(=O)$— |
| II-3 | —$CH(CH_3)$— |
| II-4 | —$C(CH_3)_2$— |
| II-5 | —$CH(C_2H_5)$— |
| II-6 | —CHCN— |
| II-7 | —$CH(CH_2OH)$— |

In the compounds I according to the invention, $R^1$ and $R^2$ independently of each other are preferably selected from the group consisting of hydrogen, halogen, CN, $C_1$-$C_4$-alkyl, $C_1$-$C_4$-haloalkyl, $C_1$-$C_4$-alkoxy, $C_1$-$C_4$-haloalkoxy and $C_3$-$C_8$-cycloalkyl; more preferably $R^1$ and $R^2$ independently of each other are hydrogen, CN, $CH_3$, $CH_2CH_3$, F, Cl or $OCH_3$; another more preferred embodiment relates to compounds I wherein $R^1$ and $R^2$ independently of each other are hydrogen or $CH_3$; more preferably $R^1$ and $R^2$ are hydrogen.

Further preferred embodiments relate to compounds I wherein $R^1$ and $R^2$ in each case are one of the following combinations III-1 to III-7 in table III:

TABLE III

| No. | $R^1$ | $R^2$ |
|---|---|---|
| III-1 | H | H |
| III-2 | $CH_3$ | H |
| III-3 | CN | H |
| III-4 | F | H |
| III-5 | Cl | H |
| III-6 | $OCH_3$ | H |
| III-7 | $CH_3$ | $CH_3$ |

In the compounds I according to the invention, $R^b$ is preferably selected from the group consisting of halogen, CN, $NO_2$, $C_1$-$C_4$-alkoxy, $C_1$-$C_4$-haloalkoxy and $C_1$-$C_4$-alkoxy-$C_1$-$C_4$-alkyl; more preferably $R^b$ is selected from the group consisting of halogen, CN, $C_1$-$C_4$-haloalkyl and $C_1$-$C_4$-alkoxy; most preferably $R^b$ is halogen, CN, $CH_3$, $CF_3$, $OCH_3$.

In the compounds I according to the invention, n is preferably 0.

A further embodiment relates to compounds I wherein n is preferably 1.

A further embodiment relates to compounds I wherein n is preferably 2.

A further embodiment relates to compounds I wherein n is preferably 3.

A further embodiment relates to compounds I wherein n is preferably 4.

In the compounds I according to the invention, Het is preferably selected from the group consisting of pyrimidin-2-yl, pyrimidin-3-yl, pyrimidin-4-yl, pyridin-2-yl, pyridin-3-yl, pyridin-4-yl, thiazol-2-yl, thiazol-4-yl, thiazol-5-yl, isothiazol-3-yl, isothiazol-4-yl, isothiazol-5-yl, pyrazin-2-yl, pyridazin-3-yl, 1,3,5-triazin-2-yl, and 1,2,4-triazin-3-yl; more preferably Het is selected from pyrimidin-2-yl, pyrimidin-3-yl, pyrimidin-4-yl, pyridin-2-yl, pyridin-3-yl, pyridin-4-yl, thiazol-2-yl, pyrazin-2-yl, pyridazin-3-yl, 1,3,5-triazin-2-yl, and 1,2,4-triazin-3-yl; preferably Het is pyrimidin-2-yl, pyridin-2-yl, pyridin-3-yl, pyridin-4-yl, thiazol-2-yl; more preferably Het is unsubstituted; a further preferred embodiment relates to compounds I wherein Het is substituted by 1 radical $R^c$; another preferred embodiment relates to compounds I wherein Het is substituted by 2 radicals $R^c$; yet another preferred embodiment relates to compounds I wherein Het is substituted by 3 radicals $R^c$; another preferred embodiment relates to compounds I wherein Het is substituted by 4 radicals R.

Preferred embodiments of the invention relate to compounds I, in which the group Het is one of the following radicals H-1 to H-38 in table H:

TABLE H

| No. | Het |
|---|---|
| H-1 | 4-$CF_3$-pyridin-2-yl |
| H-2 | 2-$CF_3$-pyridin-4-yl |
| H-3 | 5-$CF_3$-pyridin-2-yl |
| H-4 | 6-$CF_3$-pyridin-2-yl |
| H-5 | 3-$CF_3$-pyridin-2-yl |

TABLE H-continued
| No. | Het |
|---|---|
| H-6 | 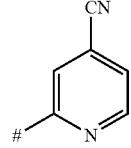 |
| H-7 | 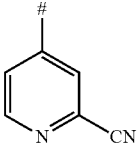 |
| H-8 | 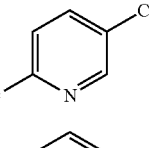 |
| H-9 | 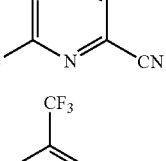 |
| H-10 | 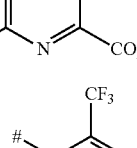 |
| H-11 | 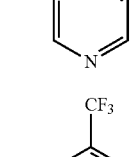 |
| H-12 | 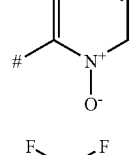 |
| H-13 | 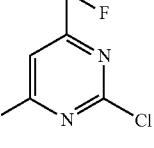 |
| H-14 | 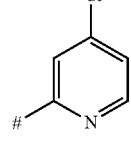 |
| H-15 | 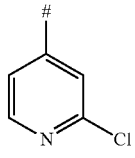 |
| H-16 | 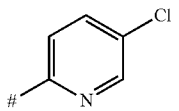 |
| H-17 | 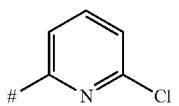 |
| H-18 | 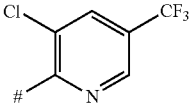 |
| H-19 | 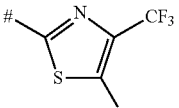 |
| H-20 | 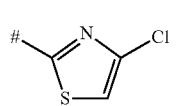 |
| H-21 | 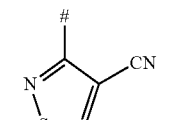 |
| H-22 | 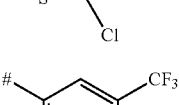 |
| H-23 | 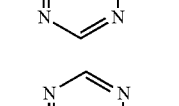 |
| H-24 | 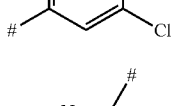 |
| H-25 | 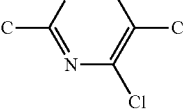 |
| H-26 | 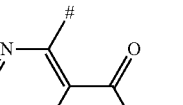 | in which # indicates the point of attachment.

In the compounds I according to the invention, $R^c$ is preferably selected from the group consisting of halogen, CN, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-alkynyl, C(=O)R', C(=NOR'')R''', $C_3$-$C_8$-cycloalkyl, phenyl and phenoxy. A further embodiment relates to compounds I wherein $R^c$ is F, Cl, CN, $CH_3$, $OCH_3$, $CF_3$, $OCF_3$ or $COOCH_3$; most preferably $R^c$ is Cl, CN, $CF_3$.

With respect to their use, particular preference is given to the compounds I.A:

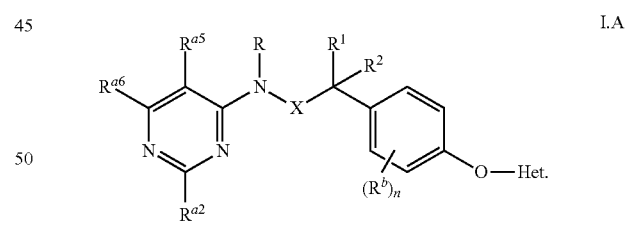

I.A

With respect to their use, particular preference is also given to the compounds I.B:

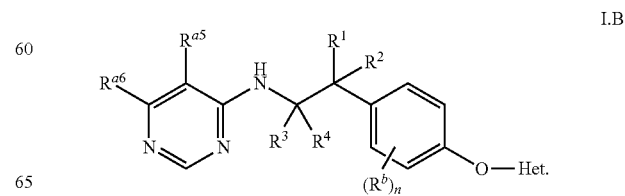

I.B

With respect to their use, particular preference is also given to the compounds I.C:

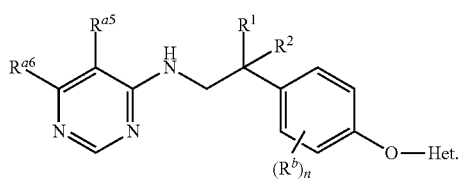

According to a further embodiment, the present invention relates to compounds of the formula I.A wherein:
$R^{a2}$, $R^{a5}$ independently of each other are hydrogen, halogen, CN, $NH_2$, $C_1$-$C_4$-alkyl, $C_1$-$C_4$-haloalkyl, $C_1$-$C_4$-alkoxy, $C_1$-$C_4$-haloalkoxy or ($C_1$-$C_4$-alkoxy)carbonyl;
$R^{a6}$ is halogen;
R is hydrogen or $C_1$-$C_4$-alkyl;
X is a divalent group —$CR^3R^4$—; wherein
  $R^3$, $R^4$ independently of each other are hydrogen, $C_1$-$C_4$-alkyl, $C_1$-$C_4$-hydroxyalkyl, $C_1$-$C_4$-alkoxy-$C_1$-$C_4$-alkyl or ($C_1$-$C_4$-alkoxy)carbonyl;
$R^1$, $R^2$ independently of each other are hydrogen or $C_1$-$C_4$-alkyl;
n indicates the number of substituents $R^b$ on the phenyl ring and n is 0 or 1;
$R^b$ is halogen, $C_1$-$C_4$-alkyl or $C_1$-$C_4$-alkoxy;
Het is a pyridinyl or pyrimidinyl wherein the pyridinyl or pyrimidinyl is unsubstituted or carries 1 or 2 groups $R^c$:
  $R^c$ is halogen, CN, $C_1$-$C_6$-alkyl, $C_1$-$C_6$-haloalkyl, $C_1$-$C_6$-alkoxy or $C_1$-$C_6$-haloalkoxy; and
the N-oxides and the agriculturally acceptable salts of the compounds of formula I.A.

The compounds I and the compositions according to the invention, respectively, are suitable as fungicides. They are distinguished by an outstanding effectiveness against a broad spectrum of phytopathogenic fungi, including soil-borne fungi, which derive especially from the classes of the Plasmodiophoromycetes, Peronosporomycetes (syn. Oomycetes), Chytridiomycetes, Zygomycetes, Ascomycetes, Basidiomycetes and Deuteromycetes (syn. *Fungi imperfecti*). Some are systemically effective and they can be used in crop protection as foliar fungicides, fungicides for seed dressing and soil fungicides. Moreover, they are suitable for controlling harmful fungi, which inter alia occur in wood or roots of plants.

The compounds I and the compositions according to the invention are particularly important in the control of a multitude of phytopathogenic fungi on various cultivated plants, such as cereals, e.g. wheat, rye, barley, triticale, oats or rice; beet, e.g. sugar beet or fodder beet; fruits, such as pomes, stone fruits or soft fruits, e.g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; sweet leaf (also called Stevia); natural rubber plants or ornamental and forestry plants, such as flowers, shrubs, broad-leaved trees or evergreens, e.g. conifers; and on the plant propagation material, such as seeds, and the crop material of these plants. Preferably, compounds I and compositions thereof, respectively are used for controlling a multitude of fungi on field crops, such as potatoes sugar beets, tobacco, wheat, rye, barley, oats, rice, corn, cotton, soybeans, rape, legumes, sunflowers, coffee or sugar cane; fruits; vines; ornamentals; or vegetables, such as cucumbers, tomatoes, beans or squashes.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil.

These young plants may also be protected before transplantation by a total or partial treatment by immersion or pouring.

Preferably, treatment of plant propagation materials with compounds I and compositions thereof, respectively, is used for controlling a multitude of fungi on cereals, such as wheat, rye, barley and oats; rice, corn, cotton and soybeans.

The term "cultivated plants" is to be understood as including plants which have been modified by breeding, mutagenesis or genetic engineering including but not limiting to agricultural biotech products on the market or in development (cf. http://www.bio.org/speeches/pubs/er/agri_products.asp).
Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein(s), oligo- or polypeptides e.g. by glycosylation or polymer additions such as prenylated, acetylated or farnesylated moieties or PEG moieties.

The compounds I and compositions thereof, respectively, are particularly suitable for controlling the following plant diseases:
*Albugo* spp. (white rust) on ornamentals, vegetables (e.g. *A. candida*) and sunflowers (e.g. *A. tragopogonis*); *Alternaria* spp. (*Alternaria* leaf spot) on vegetables, rape (*A. brassicola* or *brassicae*), sugar beets (*A. tenuis*), fruits, rice, soybeans, potatoes (e.g. *A. solani* or *A. alternata*), tomatoes (e.g. *A. solani* or *A. alternata*) and wheat; *Aphanomyces* spp. on sugar beets and vegetables; *Ascochyta* spp. on cereals and vegetables, e.g. *A. tritici* (anthracnose) on wheat and *A. hordei* on barley; *Bipolaris* and *Drechslera* spp. (teleomorph: *Cochliobolus* spp.), e.g. Southern leaf blight (*D. maydis*) or Northern leaf blight (*B. zeicola*) on corn, e.g. spot blotch (*B. sorokiniana*) on cereals and e.g. *B. oryzae* on rice and turfs; *Blumeria* (formerly *Erysiphe*) *graminis* (powdery mildew) on cereals (e.g. on wheat or barley); *Botrytis cinerea* (teleomorph: *Botryotinia fuckeliana*: grey mold) on fruits and berries (e.g. strawberries), vegetables (e.g. lettuce, carrots, celery and cabbages), rape, flowers, vines, forestry plants and wheat; *Bremia lactucae* (downy mildew) on lettuce; *Ceratocystis* (syn. *Ophiostoma*) spp. (rot or wilt) on broad-leaved trees and evergreens, e.g. *C. ulmi* (Dutch elm disease) on elms; *Cercospora* spp. (*Cercospora* leaf spots) on corn (e.g.

Gray leaf spot: *C. zeae-maydis*), rice, sugar beets (e.g. *C. beticola*), sugar cane, vegetables, coffee, soybeans (e.g. *C. sojina* or *C. kikuchii*) and rice; *Cladosporium* spp. on tomatoes (e.g. *C. fulvum*: leaf mold) and cereals, e.g. *C. herbarum* (black ear) on wheat; *Claviceps purpurea* (ergot) on cereals; *Cochliobolus* (anamorph: *Helminthosporium* of *Bipolaris*) spp. (leaf spots) on corn (*C. carbonum*), cereals (e.g. *C. sativus*, anamorph: *B. sorokiniana*) and rice (e.g. *C. miyabeanus*, anamorph: *H. oryzae*); *Colletotrichum* (teleomorph: *Glomerella*) spp. (anthracnose) on cotton (e.g. *C. gossypii*), corn (e.g. *C. graminicola*: Anthracnose stalk rot), soft fruits, potatoes (e.g. *C. coccodes*: black dot), beans (e.g. *C. lindemuthianum*) and soybeans (e.g. *C. truncatum* or *C. gloeosporioides*); *Corticium* spp., e.g. *C. sasakii* (sheath blight) on rice; *Corynespora cassiicola* (leaf spots) on soybeans and ornamentals; *Cycloconium* spp., e.g. *C. oleaginum* on olive trees; *Cylindrocarpon* spp. (e.g. fruit tree canker or young vine decline, teleomorph: *Nectria* or *Neonectria* spp.) on fruit trees, vines (e.g. *C. liriodendri*, teleomorph: *Neonectria liriodendri*: Black Foot Disease) and ornamentals; Dematophora (teleomorph: *Rosellinia*) necatrix (root and stem rot) on soybeans; *Diaporthe* spp., e.g. *D. phaseolorum* (damping off) on soybeans; *Drechslera* (syn. *Helminthosporium*, teleomorph: *Pyrenophora*) spp. on corn, cereals, such as barley (e.g. *D. teres*, net blotch) and wheat (e.g. *D. tritici-repentis*: tan spot), rice and turf; Esca (dieback, apoplexy) on vines, caused by Formitiporia (syn. *Phellinus*) punctata, *F. mediterranea*, Phaeomoniella chlamydospora (earlier Phaeoacremonium chlamydosporum), Phaeoacremonium aleophilum and/or *Botryosphaeria obtusa; Elsinoe* spp. on pome fruits (*E. pyri*), soft fruits (*E. veneta*: anthracnose) and vines (*E. ampelina*: anthracnose); *Entyloma oryzae* (leaf smut) on rice; *Epicoccum* spp. (black mold) on wheat; *Erysiphe* spp. (powdery mildew) on sugar beets (*E. betae*), vegetables (e.g. *E. pisi*), such as cucurbits (e.g. *E. cichoracearum*), cabbages, rape (e.g. *E. cruciferarum*); *Eutypa* lata (*Eutypa* canker or dieback, anamorph: *Cytosporina lata*, syn. *Libertella blepharis*) on fruit trees, vines and ornamental woods; *Exserohilum* (syn. *Helminthosporium*) spp. on corn (e.g. *E. turcicum*); *Fusarium* (teleomorph: *Gibberella*) spp. (wilt, root or stem rot) on various plants, such as *F. graminearum* or *F. culmorum* (root rot, scab or head blight) on cereals (e.g. wheat or barley), *F. oxysporum* on tomatoes, *F. solani* on soybeans and *F. verticillioides* on corn; *Gaeumannomyces graminis* (take-all) on cereals (e.g. wheat or barley) and corn; *Gibberella* spp. on cereals (e.g. *G. zeae*) and rice (e.g. *G. fujikuroi*: Bakanae disease); *Glomerella cingulata* on vines, pome fruits and other plants and *G. gossypii* on cotton; Grainstaining complex on rice; *Guignardia bidwellii* (black rot) on vines; *Gymnosporangium* spp. on rosaceous plants and junipers, e.g. *G. sabinae* (rust) on pears; *Helminthosporium* spp. (syn. *Drechslera*, teleomorph: *Cochliobolus*) on corn, cereals and rice; *Hemileia* spp., e.g. *H. vastatrix* (coffee leaf rust) on coffee; *Isariopsis clavispora* (syn. *Cladosporium vitis*) on vines; *Macrophomina phaseolina* (syn. phaseoli) (root and stem rot) on soybeans and cotton; *Microdochium* (syn. *Fusarium*) nivale (pink snow mold) on cereals (e.g. wheat or barley); *Microsphaera diffusa* (powdery mildew) on soybeans; *Monilinia* spp., e.g. *M. laxa, M. fructicola* and *M. fructigena* (bloom and twig blight, brown rot) on stone fruits and other rosaceous plants; *Mycosphaerella* spp. on cereals, bananas, soft fruits and ground nuts, such as e.g. *M. graminicola* (anamorph: *Septoria tritici, Septoria* blotch) on wheat or *M. fijiensis* (black Sigatoka disease) on bananas; *Peronospora* spp. (downy mildew) on cabbage (e.g. *P. brassicae*), rape (e.g. *P. parasitica*), onions (e.g. *P. destructor*), tobacco (*P. tabacina*) and soybeans (e.g. *P. manshurica*); *Phakopsora pachyrhizi* and *P. meibomiae* (soybean rust) on soybeans; *Phialophora* spp. e.g. on vines (e.g. *P. tracheiphila* and *P. tetraspora*) and soybeans (e.g. *P. gregata*: stem rot); *Phoma lingam* (root and stem rot) on rape and cabbage and *P. betae* (root rot, leaf spot and damping-off) on sugar beets; *Phomopsis* spp. on sunflowers, vines (e.g. *P. viticola*: can and leaf spot) and soybeans (e.g. stem rot: *P. phaseoli*, teleomorph: *Diaporthe phaseolorum*); *Physoderma maydis* (brown spots) on corn; *Phytophthora* spp. (wilt, root, leaf, fruit and stem root) on various plants, such as paprika and cucurbits (e.g. *P. capsici*), soybeans (e.g. *P. megasperma*, syn. *P. sojae*), potatoes and tomatoes (e.g. *P. infestans*: late blight) and broad-leaved trees (e.g. *P. ramorum*: sudden oak death); *Plasmodiophora brassicae* (club root) on cabbage, rape, radish and other plants; *Plasmopara* spp., e.g. *P. viticola* (grapevine downy mildew) on vines and *P. halstedii* on sunflowers; *Podosphaera* spp. (powdery mildew) on rosaceous plants, hop, pome and soft fruits, e.g. *P. leucotricha* on apples; *Polymyxa* spp., e.g. on cereals, such as barley and wheat (*P. graminis*) and sugar beets (*P. betae*) and thereby transmitted viral diseases; *Pseudocercosporella herpotrichoides* (eyespot, teleomorph: Tapesia yallundae) on cereals, e.g. wheat or barley; *Pseudoperonospora* (downy mildew) on various plants, e.g. *P. cubensis* on cucurbits or *P. humili* on hop; *Pseudopeziculla tracheiphila* (red fire disease or 'rotbrenner', anamorph: *Phialophora*) on vines; *Puccinia* spp. (rusts) on various plants, e.g. *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e.g. wheat, barley or rye, *P. kuehnii* (orange rust) on sugar cane and *P. asparagi* on asparagus; *Pyrenophora* (anamorph: *Drechslera*) tritici-repentis (tan spot) on wheat or *P. teres* (net blotch) on barley; *Pyricularia* spp., e.g. *P. oryzae* (teleomorph: *Magnaporthe grisea*, rice blast) on rice and *P. grisea* on turf and cereals; *Pythium* spp. (damping-off) on turf, rice, corn, wheat, cotton, rape, sunflowers, soybeans, sugar beets, vegetables and various other plants (e.g. *P. ultimum* or *P. aphani*-dermatum); *Ramularia* spp., e.g. *R. collo-cygni* (Ramularia leaf spots, Physiological leaf spots) on barley and *R. beticola* on sugar beets; *Rhizoctonia* spp. on cotton, rice, potatoes, turf, corn, rape, potatoes, sugar beets, vegetables and various other plants, e.g. *R. solani* (root and stem rot) on soybeans, *R. solani* (sheath blight) on rice or *R. cerealis* (*Rhizoctonia* spring blight) on wheat or barley; *Rhizopus stolonifer* (black mold, soft rot) on strawberries, carrots, cabbage, vines and tomatoes; *Rhynchosporium secalis* (scald) on barley, rye and triticale; *Sarocladium oryzae* and *S. attenuatum* (sheath rot) on rice; *Sclerotinia* spp. (stem rot or white mold) on vegetables and field crops, such as rape, sunflowers (e.g. *S. sclerotiorum*) and soybeans (e.g. *S. rolfsii* or *S. sclerotiorum*); *Septoria* spp. on various plants, e.g. *S. glycines* (brown spot) on soybeans, *S. tritici* (*Septoria* blotch) on wheat and *S.* (syn. *Stagonospora*) *nodorum* (*Stagonospora* blotch) on cereals; *Uncinula* (syn. *Erysiphe*) necator (powdery mildew, anamorph: *Oidium tuckeri*) on vines; *Setosphaeria* spp. (leaf blight) on corn (e.g. *S. turcicum*, syn. *Helminthosporium turcicum*) and turf; *Sphacelotheca* spp. (smut) on corn, (e.g. *S. reiliana*: head smut), sorghum and sugar cane; *Sphaerotheca fuliginea* (powdery mildew) on cucurbits; *Spongospora subterranea* (powdery scab) on potatoes and thereby transmitted viral diseases; *Stagonospora* spp. on cereals, e.g. *S. nodorum* (*Stagonospora* blotch, teleomorph: *Leptosphaeria* [syn. *Phaeosphaeria*] *nodorum*) on wheat; *Synchytrium endobioticum* on potatoes (potato wart disease); *Taphrina* spp., e.g. *T. deformans* (leaf curl disease) on peaches and *T. pruni* (plum pocket) on plums; *Thielaviopsis* spp. (black root rot) on tobacco, pome fruits, vegetables, soybeans and cotton, e.g. *T. basicola* (syn. *Chalara elegans*); *Tilletia* spp. (common bunt or stinking smut) on cereals, such as e.g. *T. tritici* (syn. *T. caries*, wheat bunt) and *T. controversa* (dwarf bunt) on wheat; *Typhula incarnata* (grey snow mold) on barley or wheat; *Urocystis* spp., e.g. *U. occulta* (stem smut) on rye; *Uromyces* spp. (rust) on vegetables, such as beans (e.g. *U. appendiculatus*, syn. *U. phaseoli*) and sugar beets (e.g. *U. betae*); *Ustilago* spp. (loose smut) on cereals (e.g. *U. nuda* and *U. avaenae*), corn (e.g. *U. maydis*: corn smut) and sugar cane; *Venturia* spp. (scab) on apples (e.g. *V. inaequalis*) and pears; and *Verticillium* spp. (wilt) on various plants, such as fruits and ornamentals, vines, soft fruits, vegetables and field crops, e.g. *V. dahliae* on strawberries, rape, potatoes and tomatoes.

The compounds I and compositions thereof, respectively, are also suitable for controlling harmful fungi in the protection of stored products or harvest and in the protection of materials. The term "protection of materials" is to be understood to denote the protection of technical and non-living materials, such as adhesives, glues, wood, paper and paperboard, textiles, leather, paint dispersions, plastics, coiling lubricants, fiber or fabrics, against the infestation and destruction by harmful microorganisms, such as fungi and bacteria. As to the protection of wood and other materials, the particular attention is paid to the following harmful fungi: Ascomycetes such as *Ophiostoma* spp., *Ceratocystis* spp., *Aureobasidium pullulans, Sclerophoma* spp., *Chaetomium* spp., *Humicola* spp., *Petriella* spp., *Trichurus* spp.; Basidiomycetes such as *Coniophora* spp., *Coriolus* spp., *Gloeophyllum* spp., *Lentinus* spp., *Pleurotus* spp., *Poria* spp., *Serpula* spp. and *Tyromyces* spp., *Deuteromycetes* such as *Aspergillus* spp., *Cladosporium* spp., *Penicillium* spp., *Trichorma* spp., *Alternaria* spp., *Paecilomyces* spp. and Zygomycetes such as *Mucor* spp., and in addition in the protection of stored products and harvest the following yeast fungi are worthy of note: *Candida* spp. and *Saccharomyces* cerevisae.

The compounds I and compositions thereof, resepectively, may be used for improving the health of a plant. The invention also relates to a method for improving plant health by treating a plant, its propagation material and/or the locus where the plant is growing or is to grow with an effective amount of compounds I and compositions thereof, respectively.

The term "plant health" is to be understood to denote a condition of the plant and/or its products which is determined by several indicators alone or in combination with each other such as yield (e.g. increased biomass and/or increased content of valuable ingredients), plant vigor (e.g. improved plant growth and/or greener leaves ("greening effect")), quality (e.g. improved content or composition of certain ingredients) and tolerance to abiotic and/or biotic stress. The above identified indicators for the health condition of a plant may be interdependent or may result from each other.

The compounds of the formula (I) can be present in different crystal modifications whose biological activity may differ. They are likewise subject matter of the present invention.

The compounds I are employed as such or in form of compositions by treating the fungi or the plants, plant propagation materials, such as seeds, soil, surfaces, materials or rooms to be protected from fungal attack with a fungicidally effective amount of the active substances. The application can be carried out both before and after the infection of the plants, plant propagation materials, such as seeds, soil, surfaces, materials or rooms by the fungi.

Plant propagation materials may be treated with compounds I as such or a composition comprising at least one compound I prophylactically either at or before planting or transplanting.

The invention also relates to agrochemical compositions comprising an auxiliary and at least one compound I according to the invention.

An agrochemical composition comprises a fungicidally effective amount of a compound I. The term "effective amount" denotes an amount of the composition or of the compounds I, which is sufficient for controlling harmful fungi on cultivated plants or in the protection of materials and which does not result in a substantial damage to the treated plants. Such an amount can vary in a broad range and is dependent on various factors, such as the fungal species to be controlled, the treated cultivated plant or material, the climatic conditions and the specific compound I used.

The compounds I, their N-oxides and salts can be converted into customary types of agrochemical compositions, e.g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Monograph No. 2, 6th Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Examples for suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e.g. toluene, paraffin, tetrahydronaphthalene, alkylated naphthalenes; alcohols, e.g. ethanol, propanol, butanol, benzylalcohol, cyclohexanol; glycols; dimethyl sulfoxide (DMSO); ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharide powders, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emusifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide.

Examples of N-substituted fatty acid amides are fatty acid glucamides or fatty acid alkanolamides. Examples of esters are fatty acid esters, glycerol esters or monoglycerides.

Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide.

Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compound I on the target.

Examples are surfactants, mineral or vegetable oils, and other auxilaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

The agrochemical compositions generally comprise between 0.01 and 95%, preferably between 0.1 and 90%, and most preferably between 0.5 and 75%, by weight of active substance. The active substances are employed in a purity of from 90% to 100%, preferably from 95% to 100% (according to NMR spectrum).

Water-soluble concentrates (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The compositions in question give, after two-to-tenfold dilution, active substance concentrations of from 0.01 to 60% by weight, preferably from 0.1 to 40%, in the ready-to-use preparations. Application can be carried out before or during sowing. Methods for applying or treating compound I and compositions thereof, respectively, on to plant propagation material, especially seeds include dressing, coating, pelleting, dusting, soaking and in-furrow application methods of the propagation material. Preferably, compound I or the compositions thereof, respectively, are applied on to the plant propagation material by a method such that germination is not induced, e.g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, in particular from 0.1 to 0.75 kg per ha.

In treatment of plant propagation materials such as seeds, e.g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seed) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and other pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank and further auxiliaries may be added, if appropriate.

Mixing the compounds I or the compositions comprising them in the use form as fungicides with other fungicides results in many cases in an expansion of the fungicidal spectrum of activity being obtained or in a prevention of fungicide resistance development. Furthermore, in many cases, synergistic effects are obtained.

The following list of active substances, in conjunction with which the compounds I can be used, is intended to illustrate the possible combinations but does not limit them:

A) Respiration inhibitors
  Inhibitors of complex III at Qo site (e.g. strobilurins): azoxystrobin, coumethoxy-strobin, coumoxystrobin, dimoxystrobin, enestroburin, fenaminstrobin, fenoxystrobin/flufenoxystrobin, fluoxastrobin, kresoxim-methyl, metominostrobin, orysastrobin, picoxystrobin, pyraclostrobin, pyrametostrobin, pyraoxystrobin, trifloxystrobin, 2-[2-(2,5-dimethyl-phenoxymethyl)-phenyl]-3-methoxy-acrylic acid methyl ester and 2-(2-(3-(2,6-di-chlorophenyl)-1-methyl-allylideneaminooxymethyl)-phenyl)-2-methoxyimino-N-methyl-acetamide, pyribencarb, triclopyricarb/chlorodincarb, famoxadone, fenamidone;
  inhibitors of complex III at Qi site: cyazofamid, amisulbrom, [(3S,6S,7R,8R)-8-benzyl-3-[(3-acetoxy-4-methoxy-pyridine-2-carbonyl)amino]-6-methyl-4,9-dioxo-1,5-dioxonan-7-yl]2-methylpropanoate, [(3S,6S,7R,8R)-8-benzyl-3-[[3-(acetoxymethoxy)-4-methoxy-pyridine-2-carbonyl]amino]-6-methyl-4,9-dioxo-1,5-dioxonan-7-yl]2-methylpropanoate, [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl]2-methylpropanoate, [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl]2-methylpropanoate;
  inhibitors of complex II (e.g. carboxamides): benodanil, bixafen, boscalid, carboxin, fenfuram, fluopyram, flutolanil, fluxapyroxad, furametpyr, isopyrazam, mepronil, oxycarboxin, penflufen, penthiopyrad, sedaxane, tecloftalam, thifluzamide, N-(4'-trifluoromethylthiobiphenyl-2-yl)-3-difluoromethyl-1-methyl-1H-pyrazole-4-carboxamide, N-(2-(1,3,3-trimethyl-butyl)-phenyl)-1,3-dimethyl-5-fluoro-1H-pyrazole-4-carboxamide, N-[9-(dichloromethylene)-1,2,3,4-tetrahydro-1,4-methanonaphthalen-5-yl]-3-(difluoromethyl)-1-methyl-1H-pyrazole-4-carboxamide;
  other respiration inhibitors (e.g. complex I, uncouplers): diflumetorim, (5,8-difluoro-quinazolin-4-yl)-{2-[2-fluoro-4-(4-trifluoromethylpyridin-2-yloxy)-phenyl]-ethyl}-amine; nitrophenyl derivates: binapacryl, dinobuton, dinocap, fluazinam; ferimzone; organometal compounds: fentin salts, such as fentin-acetate, fentin chloride or fentin hydroxide; ametoctradin; and silthiofam;

B) Sterol biosynthesis inhibitors (SBI fungicides)
  C14 demethylase inhibitors (DMI fungicides): triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole; imidazoles: imazalil, pefurazoate, prochloraz, triflumizol; pyrimidines, pyridines and piperazines: fenarimol, nuarimol, pyrifenox, triforine;
  Delta14-reductase inhibitors: aldimorph, dodemorph, dodemorph-acetate, fenpropimorph, tridemorph, fenpropidin, piperalin, spiroxamine;
  Inhibitors of 3-keto reductase: fenhexamid;

C) Nucleic acid synthesis inhibitors
  phenylamides or acyl amino acid fungicides: benalaxyl, benalaxyl-M, kiralaxyl, metalaxyl, metalaxyl-M (mefenoxam), ofurace, oxadixyl;
  others: hymexazole, octhilinone, oxolinic acid, bupirimate, 5-fluorocytosine, 5-fluoro-2-(p-tolylmethoxy)pyrimidin-4-amine, 5-fluoro-2-(4-fluorophenylmethoxy)pyrimidin-4-amine;

D) Inhibitors of cell division and cytoskeleton
  tubulin inhibitors, such as benzimidazoles, thiophanates: benomyl, carbendazim, fuberidazole, thiabendazole, thiophanate-methyl; triazolopyrimidines: 5-chloro-7-(4-methylpiperidin-1-yl)-6-(2,4,6-trifluorophenyl)-[1,2,4]triazolo[1,5-a]pyrimidine
  other cell division inhibitors: diethofencarb, ethaboxam, pencycuron, fluopicolide, zoxamide, metrafenone, pyriofenone;

E) Inhibitors of amino acid and protein synthesis
  methionine synthesis inhibitors (anilino-pyrimidines): cyprodinil, mepanipyrim, pyrimethanil;
  protein synthesis inhibitors: blasticidin-S, kasugamycin, kasugamycin hydrochloride-hydrate, mildiomycin, streptomycin, oxytetracyclin, polyoxine, validamycin A;

F) Signal transduction inhibitors
  MAP/histidine kinase inhibitors: fluoroimid, iprodione, procymidone, vinclozolin, fenpiclonil, fludioxonil;
  G protein inhibitors: quinoxyfen;

G) Lipid and membrane synthesis inhibitors
  Phospholipid biosynthesis inhibitors: edifenphos, iprobenfos, pyrazophos, isoprothiolane;
  lipid peroxidation: dicloran, quintozene, tecnazene, tolclofos-methyl, biphenyl, chloroneb, etridiazole;
  phospholipid biosynthesis and cell wall deposition: dimethomorph, flumorph, mandipropamid, pyrimorph, benthiavalicarb, iprovalicarb, valifenalate and N-(1-(1-(4-cyano-phenyl)ethanesulfonyl)-but-2-yl) carbamic acid-(4-fluorophenyl) ester;
  compounds affecting cell membrane permeability and fatty acides: propamocarb, propamocarb-hydrochlorid H) Inhibitors with Multi Site Action
  inorganic active substances: Bordeaux mixture, copper acetate, copper hydroxide, copper oxychloride, basic copper sulfate, sulfur;
  thio- and dithiocarbamates: ferbam, mancozeb, maneb, metam, metiram, propineb, thiram, zineb, ziram;
  organochlorine compounds (e.g. phthalimides, sulfamides, chloronitriles): anilazine, chlorothalonil, captafol, captan, folpet, dichlofluanid, dichlorophen, flusulfamide, hexachlorobenzene, pentachlorphenole and its salts, phthalide, tolylfluanid, N-(4-chloro-2-nitro-phenyl)-N-ethyl-4-methyl-benzenesulfonamide;
  guanidines and others: guanidine, dodine, dodine free base, guazatine, guazatine-acetate, iminoctadine, iminoctadine-triacetate, iminoctadine-tris(albesilate), dithianon;

I) Cell wall synthesis inhibitors
   inhibitors of glucan synthesis: validamycin, polyoxin B;
   melanin synthesis inhibitors:
   pyroquilon, tricyclazole, carpropamid, dicyclomet, fenoxanil;
J) Plant defence inducers
   acibenzolar-5-methyl, probenazole, isotianil, tiadinil, prohexadione-calcium;
   phosphonates: fosetyl, fosetyl-aluminum, phosphorous acid and its salts;
K) Unknown mode of action
   bronopol, chinomethionat, cyflufenamid, cymoxanil, dazomet, debacarb, diclo-mezine, difenzoquat, difenzoquat-methylsulfate, diphenylamin, fenpyrazamine, flumetover, flusulfamide, flutianil, methasulfocarb, nitrapyrin, nitrothal-isopropyl, oxin-copper, proquinazid, tebufloquin, tecloftalam, triazoxide, 2-butoxy-6-iodo-3-propylchromen-4-one, N-(cyclopropyl-methoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2-methyl-4-(3-trimethylsilanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide, 2-{1-[2-(5-methyl-3-trifluoromethyl-pyrazole-1-yl)-acetyl]piperidin-4-yl}-thiazole-4-carboxylic acid methyl-(R)-1,2,3,4-tetrahydro-naphthalen-1-yl-amide, 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone, methoxy-acetic acid 6-tert-butyl-8-fluoro-2,3-dimethyl-quinolin-4-yl ester, N-Methyl-2-{1-[(5-methyl-3-trifluoromethyl-1H-pyrazol-1-yl)-acetyl]-piperidin-4-yl}-N-[(1R)-1,2,3,4-tetrahydronaphthalen-1-yl]-4-thiazolecarboxamide, 3-[5-(4-methylphenyl)-2,3-dimethyl-isoxazolidin-3-yl]pyridine, 3-[5-(4-chloro-phenyl)-2,3-dimethyl-isoxazolidin-3-yl]-pyridine (pyrisoxazole), N-(6-methoxy-pyridin-3-yl)cyclopropanecarboxylic acid amide, 5-chloro-1-(4,6-dimethoxy-pyrimidin-2-yl)-2-methyl-1H-benzoimidazole, 2-(4-chloro-phenyl)-N-[4-(3,4-dimethoxy-phenyl)-isoxazol-5-yl]-2-prop-2-ynyloxy-acetamide;
L) Antifungal biocontrol agents, plant bioactivators: *Ampelomyces quisqualis* (e.g. AQ 10® from Intrachem Bio GmbH & Co. KG, Germany), *Aspergillus flavus* (e.g. AFLAGUARD® from Syngenta, CH), *Aureobasidium pullulans* (e.g. BOTECTOR® from bio-ferm GmbH, Germany), *Bacillus pumilus* (e.g. NRRL Accession No. B-30087 in SONATA® and BALLAD® Plus from AgraQuest Inc., USA), *Bacillus subtilis* (e.g. isolate NRRL-Nr. B-21661 in RHAPSODY®, SERENADE® MAX and SERENADE® ASO from AgraQuest Inc., USA), *Bacillus subtilis* var. *amyloliquefaciens* FZB24 (e.g. TAEGRO® from Novozyme Biologicals, Inc., USA), *Candida* oleophila 1-82 (e.g. ASPIRE® from Ecogen Inc., USA), *Candida saitoana* (e.g. BIOCURE® (in mixture with lysozyme) and BIOCOAT® from Micro Flo Company, USA (BASF SE) and Arysta), Chitosan (e.g. ARMOUR-ZEN from BotriZen Ltd., NZ), *Clonostachys rosea f. catenulata*, also named *Gliocladium catenulatum* (e.g. isolate J1446: PRESTOP® from Verdera, Finland), *Coniothyrium* minitans (e.g. CONTANS® from Prophyta, Germany), *Cryphonectria parasitica* (e.g. *Endothia parasitica* from CNICM, France), *Cryptococcus albidus* (e.g. YIELD PLUS® from Anchor Bio-Technologies, South Africa), *Fusarium oxysporum* (e.g. BIOFOX® from S.I.A.P.A., Italy, FUSACLEAN® from Natural Plant Protection, France), *Metschnikowia fructicola* (e.g. SHEMER® from Agrogreen, Israel), *Microdochium dimerum* (e.g. ANTIBOT® from Agrauxine, France), Phlebiopsis gigantea (e.g. ROTSOP® from Verdera, Finland), Pseudozyma flocculosa (e.g. SPORODEX® from Plant Products Co. Ltd., Canada), *Pythium oligandrum* DV74 (e.g. POLYVERSUM® from Remeslo SSRO, Biopreparaty, Czech Rep.), Reynoutria sachlinensis (e.g. REGALIA® from Marrone BioInnovations, USA), Talaromyces flavus V117b (e.g. PROTUS® from Prophyta, Germany), *Trichoderma* asperellum SKT-1 (e.g. ECO—HOPE® from Kumiai Chemical Industry Co., Ltd., Japan), *T. atroviride* LC52 (e.g. SENTINEL® from Agrimm Technologies Ltd, NZ), *T. harzianum* T-22 (e.g. PLANTSHIELD® der Firma BioWorks Inc., USA), *T. harzianum* TH 35 (e.g. ROOT PRO® from Mycontrol Ltd., Israel), *T. harzianum* T-39 (e.g. TRICHODEX® and TRICHODERMA 2000® from Mycontrol Ltd., Israel and Makhteshim Ltd., Israel), *T. harzianum* and *T. viride* (e.g. TRICHOPEL from Agrimm Technologies Ltd, NZ), *T. harzianum* ICC012 and *T. viride* ICC080 (e.g. REMEDIER® WP from Isagro Ricerca, Italy), *T. polysporum* and *T. harzianum* (e.g. BINAB® from BINAB Bio-Innovation AB, Sweden), *T. stromaticum* (e.g. TRICOVAB® from C.E.P.L.A.C., Brazil), *T. virens* GL-21 (e.g. SOILGARD® from Certis LLC, USA), *T. viride* (e.g. TRIECO® from Ecosense Labs. (India) Pvt. Ltd., Indien, BIO-CURE® F from T. Stanes & Co. Ltd., Indien), *T. viride* TV1 (e.g. *T. viride* TV1 from Agribiotec srl, Italy), Ulocladium oudemansii HRU3 (e.g. BOTRY-ZEN® from Botry-Zen Ltd, NZ);
M) Growth regulators
   abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N-6-benzyladenine, paclobutrazol, prohexadione (prohexadione-calcium), prohydrojasmon, thidiazuron, triapenthenol, tributyl phosphorotrithioate, 2,3,5-tri-iodobenzoic acid, trinexapac-ethyl and uniconazole;
N) Herbicides
   acetamides: acetochlor, alachlor, butachlor, dimethachlor, dimethenamid, flufenacet, mefenacet, metolachlor, metazachlor, napropamide, naproanilide, pethoxamid, pretilachlor, propachlor, thenylchlor;
   amino acid derivatives: bilanafos, glyphosate, glufosinate, sulfosate;
   aryloxyphenoxypropionates: clodinafop, cyhalofop-butyl, fenoxaprop, fluazifop, haloxyfop, metamifop, propaquizafop, quizalofop, quizalofop-P-tefuryl;
   Bipyridyls: diquat, paraquat;
   (thio)carbamates: asulam, butylate, carbetamide, desmedipham, dimepiperate, eptam (EPTC), esprocarb, molinate, orbencarb, phenmedipham, prosulfocarb, pyributicarb, thiobencarb, triallate;
   cyclohexanediones: butroxydim, clethodim, cycloxydim, profoxydim, sethoxydim, tepraloxydim, tralkoxydim;
   dinitroanilines: benfluralin, ethalfluralin, oryzalin, pendimethalin, prodiamine, trifluralin;

diphenyl ethers: acifluorfen, aclonifen, bifenox, diclofop, ethoxyfen, fomesafen, lactofen, oxyfluorfen;

hydroxybenzonitriles: bomoxynil, dichlobenil, ioxynil;

imidazolinones: imazamethabenz, imazamox, imazapic, imazapyr, imazaquin, imazethapyr;

phenoxy acetic acids: clomeprop, 2,4-dichlorophenoxyacetic acid (2,4-D), 2,4-DB, dichlorprop, MCPA, MCPA-thioethyl, MCPB, Mecoprop;

pyrazines: chloridazon, flufenpyr-ethyl, fluthiacet, norflurazon, pyridate;

pyridines: aminopyralid, clopyralid, diflufenican, dithiopyr, fluridone, fluoroxypyr, picloram, picolinafen, thiazopyr;

sulfonyl ureas: amidosulfuron, azimsulfuron, bensulfuron, chlorimuron-ethyl, chlorsulfuron, cinosulfuron, cyclosulfamuron, ethoxysulfuron, flazasulfuron, flucetosulfuron, flupyrsulfuron, foramsulfuron, halosulfuron, imazosulfuron, iodosulfuron, mesosulfuron, metazosulfuron, metsulfuron-methyl, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, 1-((2-chloro-6-propyl-imidazo[1,2-b]pyridazin-3-yOsulfonyl)-3-(4,6-dimethoxy-pyrimidin-2-yl)urea;

triazines: ametryn, atrazine, cyanazine, dimethametryn, ethiozin, hexazinone, metamitron, metribuzin, prometryn, simazine, terbuthylazine, terbutryn, triaziflam;

ureas: chlorotoluron, daimuron, diuron, fluometuron, isoproturon, linuron, metha-benzthiazuron, tebuthiuron;

other acetolactate synthase inhibitors: bispyribac-sodium, cloransulam-methyl, diclosulam, florasulam, flucarbazone, flumetsulam, metosulam, ortho-sulfamuron, penoxsulam, propoxycarbazone, pyribambenz-propyl, pyribenzoxim, pyriftalid, pyriminobac-methyl, pyrimisulfan, pyrithiobac, pyroxasulfone, pyroxsulam;

others: amicarbazone, aminotriazole, anilofos, beflubutamid, benazolin, bencarbazone, benfluresate, benzofenap, bentazone, benzobicyclon, bicyclopyrone, bromacil, bromobutide, butafenacil, butamifos, cafenstrole, carfentrazone, cinidon-ethyl, chlorthal, cinmethylin, clomazone, cumyluron, cyprosulfamide, dicamba, difenzoquat, diflufenzopyr, *Drechslera monoceras*, endothal, ethofumesate, etobenzanid, fenoxasulfone, fentrazamide, flumiclorac-pentyl, flumioxazin, flupoxam, fluorochloridone, flurtamone, indanofan, isoxaben, isoxaflutole, lenacil, propanil, propyzamide, quinclorac, quinmerac, mesotrione, methyl arsonic acid, naptalam, oxadiargyl, oxadiazon, oxaziclomefone, pentoxazone, pinoxaden, pyraclonil, pyraflufen-ethyl, pyrasulfotole, pyrazoxyfen, pyrazolynate, quinoclamine, saflufenacil, sulcotrione, sulfentrazone, terbacil, tefuryltrione, tembotrione, thiencarbazone, topramezone, (3-[2-chloro-4-fluoro-5-(3-methyl-2,6-dioxo-4-trifluoromethyl-3,6-dihydro-2H-pyrimidin-1-yl)-phenoxy]-pyridin-2-yloxy)-acetic acid ethyl ester, 6-amino-5-chloro-2-cyclopropyl-pyrimidine-4-carboxylic acid methyl ester, 6-chloro-3-(2-cyclopropyl-6-methyl-phenoxy)-pyridazin-4-ol, 4-amino-3-chloro-6-(4-chloro-phenyl)-5-fluoro-pyridine-2-carboxylic acid, 4-amino-3-chloro-6-(4-chloro-2-fluoro-3-methoxy-phenyl)-pyridine-2-carboxylic acid methyl ester, and 4-amino-3-chloro-6-(4-chloro-3-dimethylamino-2-fluoro-phenyl)-pyridine-2-carboxylic acid methyl ester.

O) Insecticides organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;

pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin;

insect growth regulators: a) chitin synthesis inhibitors: benzoylureas: chlorfluazuron, cyramazin, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat;

nicotinic receptor agonists/antagonists compounds: clothianidin, dinotefuran, imidacloprid, thiamethoxam, nitenpyram, acetamiprid, thiacloprid, 1-(2-chloro-thiazol-5-ylmethyl)-2-nitrimino-3,5-dimethyl-[1,3,5]triazinane;

GABA antagonist compounds: endosulfan, ethiprole, fipronil, vaniliprole, pyrafluprole, pyriprole, 5-amino-1-(2,6-dichloro-4-methyl-phenyl)-4-sulfinamoyl-1H-pyrazole-3-carbothioic acid amide;

macrocyclic lactone insecticides: abamectin, emamectin, milbemectin, lepimectin, spinosad, spinetoram;

mitochondrial electron transport inhibitor (METI) I acaricides: fenazaquin, pyridaben, tebufenpyrad, tolfenpyrad, flufenerim;

METI II and III compounds: acequinocyl, fluacyprim, hydramethylnon;

Uncouplers: chlorfenapyr;

oxidative phosphorylation inhibitors: cyhexatin, diafenthiuron, fenbutatin oxide, propargite;

moulting disruptor compounds: cryomazine;

mixed function oxidase inhibitors: piperonyl butoxide;

sodium channel blockers: indoxacarb, metaflumizone;

others: benclothiaz, bifenazate, cartap, flonicamid, pyridalyl, pymetrozine, sulfur, thiocyclam, flubendiamide, chlorantraniliprole, cyazypyr (HGW86), cyenopyrafen, flupyrazofos, cyflumetofen, amidoflumet, imicyafos, bistrifluoron, pyrifluquinazon and 1,1'-[(3S,4R,4aR,6S,6aS,12R,12aS,12bS)-4-[[(2-cyclopropylacetyl)oxy]methyl]-1,3,4,4a,5,6,6a,12,12a,12b-decahydro-12-hydroxy-4,6a,12b-trimethyl-1'-oxo-9-(3-pyridinyl)-2H,11H-naphtho[2,1-b]pyrano[3,4-e]pyran-3,6-diyl] cyclopropaneacetic acid ester.

The present invention furthermore relates to agrochemical compositions comprising a mixture of at least one compound I (component 1) and at least one further active substance useful for plant protection, e.g. selected from the groups A) to O) (component 2), in particular one further fungicide, e.g. one or more fungicide from the groups A) to L), as described above, and if desired one suitable solvent or solid carrier. Those mixtures are of particular interest, since many of them at the same application rate show higher efficiencies against harmful fungi. Furthermore, combating harmful fungi with a mixture of compounds I and at least one fungicide from groups A) to L), as described above, is more efficient than combating those fungi with individual compounds I or individual fungicides from groups A) to L). By applying compounds I together with at least one active substance from groups A) to O) a synergistic effect can be obtained, i.e. more then simple addition of the individual effects is obtained (synergistic mixtures).

This can be obtained by applying the compounds I and at least one further active substance simultaneously, either jointly (e.g. as tank-mix) or separately, or in succession, wherein the time interval between the individual applications is selected to ensure that the active substance applied first still occurs at the site of action in a sufficient amount at the time of application of the further active substance(s). The order of application is not essential for working of the present invention.

In binary mixtures, i.e. compositions according to the invention comprising one compound I (component 1) and one further active substance (component 2), e.g. one active substance from groups A) to O), the weight ratio of component 1 and component 2 generally depends from the properties of the active substances used, usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:3 to 3:1. In ternary mixtures, i.e. compositions according to the invention comprising one compound I (component 1) and a first further active substance (component 2) and a second further active substance (component 3), e.g. two active substances from groups A) to O), the weight ratio of component 1 and component 2 depends from the properties of the active substances used, preferably it is in the range of from 1:50 to 50:1 and particularly in the range of from 1:10 to 10:1, and the weight ratio of component 1 and component 3 preferably is in the range of from 1:50 to 50:1 and particularly in the range of from 1:10 to 10:1.

Preference is also given to mixtures comprising a compound I (component 1) and at least one active substance selected from group A) (component 2) and particularly selected from azoxystrobin, dimoxystrobin, fluoxastrobin, kresoxim-methyl, orysastrobin, picoxystrobin, pyraclostrobin, trifloxystrobin; famoxadone, fenamidone; bixafen, boscalid, fluopyram, fluxapyroxad, isopyrazam, penflufen, penthiopyrad, sedaxane; ametoctradin, cyazofamid, fluazinam, fentin salts, such as fentin acetate.

Preference is given to mixtures comprising a compound I (component 1) and at least one active substance selected from group B) (component 2) and particularly selected from cyproconazole, difenoconazole, epoxiconazole, fluquinconazole, flusilazole, flutriafol, metconazole, myclobutanil, penconazole, propiconazole, prothioconazole, triadimefon, triadimenol, tebuconazole, tetraconazole, triticonazole, prochloraz, fenarimol, triforine; dodemorph, fenpropimorph, tridemorph, fenpropidin, spiroxamine; fenhexamid.

Preference is given to mixtures comprising a compound I (component 1) and at least one active substance selected from group C) (component 2) and particularly selected from metalaxyl, (metalaxyl-M) mefenoxam, ofurace.

Preference is given to mixtures comprising a compound I (component 1) and at least one active substance selected from group D) (component 2) and particularly selected from benomyl, carbendazim, thiophanate-methyl, ethaboxam, fluopicolide, zoxamide, metrafenone, pyriofenone.

Preference is also given to mixtures comprising a compound I (component 1) and at least one active substance selected from group E) (component 2) and particularly selected from cyprodinil, mepanipyrim, pyrimethanil.

Preference is also given to mixtures comprising a compound I (component 1) and at least one active substance selected from group F) (component 2) and particularly selected from iprodione, fludioxonil, vinclozolin, quinoxyfen.

Preference is also given to mixtures comprising a compound I (component 1) and at least one active substance selected from group G) (component 2) and particularly selected from dimethomorph, flumorph, iprovalicarb, benthiavalicarb, mandipropamid, propamocarb.

Preference is also given to mixtures comprising a compound I (component 1) and at least one active substance selected from group H) (component 2) and particularly selected from copper acetate, copper hydroxide, copper oxychloride, copper sulfate, sulfur, mancozeb, metiram, propineb, thiram, captafol, folpet, chlorothalonil, dichlofluanid, dithianon.

Preference is also given to mixtures comprising a compound I (component 1) and at least one active substance selected from group I) (component 2) and particularly selected from carpropamid and fenoxanil.

Preference is also given to mixtures comprising a compound I (component 1) and at least one active substance selected from group J) (component 2) and particularly selected from acibenzolar-5-methyl, probenazole, tiadinil, fosetyl, fosetyl-aluminium, $H_3PO_3$ and salts thereof.

Preference is also given to mixtures comprising a compound I (component 1) and at least one active substance selected from group K) (component 2) and particularly selected from cymoxanil, proquinazid and N-methyl-2-{1-[(5-methyl-3-trifluoromethyl-1H-pyrazol-1-yl)-acetyl]-piperidin-4-yl}-N-[(1R)-1,2,3,4-tetrahydronaphthalen-1-yl]-4-thiazolecarboxamide.

Preference is also given to mixtures comprising a compound I (component 1) and at least one active substance selected from group L) (component 2) and particularly selected from *Bacillus subtilis* strain NRRL No. B-21661, *Bacillus pumilus* strain NRRL No. B-30087 and Ulocladium oudemansii.

Accordingly, the present invention furthermore relates to compositions comprising one compound I (component 1) and one further active substance (component 2), which further active substance is selected from the column "Component 2" of the lines D-1 to D-370 of Table D.

A further embodiment relates to the compositions D-1 to D-370 listed in Table D, where a row of Table D corresponds in each case to a fungicidal composition comprising one of the in the present specification individualized compounds of formula I (component 1) and the respective further active substance from groups A) to O) (component 2) stated in the row in question.

Preferably, the compositions described comprise the active substances in synergistically effective amounts.

TABLE D

Composition comprising one indiviualized compound I
and one further active substance from groups A) to O)

| Mixture | Component 1 | Component 2 |
|---|---|---|
| D-1 | one individualized compound I | Azoxystrobin |
| D-2 | one individualized compound I | Coumethoxystrobin |
| D-3 | one individualized compound I | Coumoxystrobin |
| D-4 | one individualized compound I | Dimoxystrobin |
| D-5 | one individualized compound I | Enestroburin |
| D-6 | one individualized compound I | Fenaminstrobin |
| D-7 | one individualized compound I | Fenoxystrobin/Flufenoxystrobin |
| D-8 | one individualized compound I | Fluoxastrobin |
| D-9 | one individualized compound I | Kresoxim-methyl |
| D-10 | one individualized compound I | Metominostrobin |
| D-11 | one individualized compound I | Orysastrobin |
| D-12 | one individualized compound I | Picoxystrobin |
| D-13 | one individualized compound I | Pyraclostrobin |
| D-14 | one individualized compound I | Pyrametostrobin |
| D-15 | one individualized compound I | Pyraoxystrobin |
| D-16 | one individualized compound I | Pyribencarb |
| D-17 | one individualized compound I | Trifloxystrobin |
| D-18 | one individualized compound I | Triclopyricarb/Chlorodincarb |
| D-19 | one individualized compound I | 2-[2-(2,5-dimethyl-phenoxymethyl)-phenyl]-3-methoxy-acrylic acid methyl ester |
| D-20 | one individualized compound I | 2-(2-(3-(2,6-dichlorophenyl)-1-methyl-allylideneaminooxymethyl)-phenyl)-2-methoxyimino-N-methyl-acetamide |
| D-21 | one individualized compound I | Benalaxyl |
| D-22 | one individualized compound I | Benalaxyl-M |
| D-23 | one individualized compound I | Benodanil |
| D-24 | one individualized compound I | Benzovindiflupyr |
| D-25 | one individualized compound I | Bixafen |
| D-26 | one individualized compound I | Boscalid |
| D-27 | one individualized compound I | Carboxin |
| D-28 | one individualized compound I | Fenfuram |
| D-29 | one individualized compound I | Fenhexamid |
| D-30 | one individualized compound I | Flutolanil |
| D-31 | one individualized compound I | Fluxapyroxad |
| D-32 | one individualized compound I | Furametpyr |
| D-33 | one individualized compound I | Isopyrazam |
| D-34 | one individualized compound I | Isotianil |
| D-35 | one individualized compound I | Kiralaxyl |
| D-36 | one individualized compound I | Mepronil |
| D-37 | one individualized compound I | Metalaxyl |
| D-38 | one individualized compound I | Metalaxyl-M |
| D-39 | one individualized compound I | Ofurace |
| D-40 | one individualized compound I | Oxadixyl |
| D-41 | one individualized compound I | Oxycarboxin |
| D-42 | one individualized compound I | Penflufen |
| D-43 | one individualized compound I | Penthiopyrad |
| D-44 | one individualized compound I | Sedaxane |
| D-45 | one individualized compound I | Tecloftalam |
| D-46 | one individualized compound I | Thifluzamide |
| D-47 | one individualized compound I | Tiadinil |
| D-48 | one individualized compound I | 2-Amino-4-methyl-thiazole-5-carboxylic acid anilide |
| D-49 | one individualized compound I | N-(4'-trifluoromethylthiobiphenyl-2-yl)-3-difluoromethyl-1-methyl-1H-pyrazole-4-carboxamide |
| D-50 | one individualized compound I | N-(2-(1,3,3-trimethyl-butyl)-phenyl)-1,3-dimethyl-5-fluoro-1H-pyrazole-4-carboxamide |
| D-51 | one individualized compound I | 3-(difluoromethyl)-1-methyl-N-(1,1,3-tri-methylindan-4-yl)pyrazole-4-carboxamide |
| D-52 | one individualized compound I | 3-(trifluoromethyl)-1-methyl-N-(1,1,3-tri-methylindan-4-yl)pyrazole-4-carboxamide |
| D-53 | one individualized compound I | 1,3-dimethyl-N-(1,1,3-trimethylindan-4-yl)pyrazole-4-carboxamide |
| D-54 | one individualized compound I | 3-(trifluoromethyl)-1,5-dimethyl-N-(1,1,3-trimethylindan-4-yl)pyrazole-4-carboxamide |
| D-55 | one individualized compound I | 3-(difluoromethyl)-1,5-dimethyl-N-(1,1,3-trimethylindan-4-yl)pyrazole-4-carboxamide |
| D-56 | one individualized compound I | 1,3,5-trimethyl-N-(1,1,3-trimethylindan-4-yl)pyrazole-4-carboxamide |

TABLE D-continued

Composition comprising one indiviualized compound I and one further active substance from groups A) to O)

| Mixture | Component 1 | Component 2 |
|---|---|---|
| D-57 | one individualized compound I | Dimethomorph |
| D-58 | one individualized compound I | Flumorph |
| D-59 | one individualized compound I | Pyrimorph |
| D-60 | one individualized compound I | Flumetover |
| D-61 | one individualized compound I | Fluopicolide |
| D-62 | one individualized compound I | Fluopyram |
| D-63 | one individualized compound I | Zoxamide |
| D-64 | one individualized compound I | Carpropamid |
| D-65 | one individualized compound I | Diclocymet |
| D-66 | one individualized compound I | Mandipropamid |
| D-67 | one individualized compound I | Oxytetracyclin |
| D-68 | one individualized compound I | Silthiofam |
| D-69 | one individualized compound I | N-(6-methoxy-pyridin-3-yl) cyclopropanecarboxylic acid amide |
| D-70 | one individualized compound I | Azaconazole |
| D-71 | one individualized compound I | Bitertanol |
| D-72 | one individualized compound I | Bromuconazole |
| D-73 | one individualized compound I | Cyproconazole |
| D-74 | one individualized compound I | Difenoconazole |
| D-75 | one individualized compound I | Diniconazole |
| D-76 | one individualized compound I | Diniconazole-M |
| D-77 | one individualized compound I | Epoxiconazole |
| D-78 | one individualized compound I | Fenbuconazole |
| D-79 | one individualized compound I | Fluquinconazole |
| D-80 | one individualized compound I | Flusilazole |
| D-81 | one individualized compound I | Flutriafol |
| D-82 | one individualized compound I | Hexaconazol |
| D-83 | one individualized compound I | Imibenconazole |
| D-84 | one individualized compound I | Ipconazole |
| D-85 | one individualized compound I | Metconazole |
| D-86 | one individualized compound I | Myclobutanil |
| D-87 | one individualized compound I | Oxpoconazol |
| D-88 | one individualized compound I | Paclobutrazol |
| D-89 | one individualized compound I | Penconazole |
| D-90 | one individualized compound I | Propiconazole |
| D-91 | one individualized compound I | Prothioconazole |
| D-92 | one individualized compound I | Simeconazole |
| D-93 | one individualized compound I | Tebuconazole |
| D-94 | one individualized compound I | Tetraconazole |
| D-95 | one individualized compound I | Triadimefon |
| D-96 | one individualized compound I | Triadimenol |
| D-97 | one individualized compound I | Triticonazole |
| D-98 | one individualized compound I | Uniconazole |
| D-99 | one individualized compound I | 1-[rel-(2S;3R)-3-(2-chlorophenyl)-2-(2,4-difluorophenyl)-oxiranylmethyl]-5-thiocyanato-1H-[1,2,4]triazole, |
| D-100 | one individualized compound I | 2-[rel-(2S;3R)-3-(2-chlorophenyl)-2-(2,4-difluorophenyl)-oxiranylmethyl]-2H-[1,2,4]triazole-3-thiol |
| D-101 | one individualized compound I | Cyazofamid |
| D-102 | one individualized compound I | Amisulbrom |
| D-103 | one individualized compound I | Imazalil |
| D-104 | one individualized compound I | Imazalil-sulfate |
| D-105 | one individualized compound I | Pefurazoate |
| D-106 | one individualized compound I | Prochloraz |
| D-107 | one individualized compound I | Triflumizole |
| D-108 | one individualized compound I | Benomyl |
| D-109 | one individualized compound I | Carbendazim |
| D-110 | one individualized compound I | Fuberidazole |
| D-111 | one individualized compound I | Thiabendazole |
| D-112 | one individualized compound I | Ethaboxam |
| D-113 | one individualized compound I | Etridiazole |
| D-114 | one individualized compound I | Hymexazole |
| D-115 | one individualized compound I | 2-(4-Chloro-phenyl)-N-[4-(3,4-di-methoxy-phenyl)-isoxazol-5-yl]-2-prop-2-yn-yloxy-acetamide |
| D-116 | one individualized compound I | Fluazinam |
| D-117 | one individualized compound I | Pyrifenox |
| D-118 | one individualized compound I | 3-[5-(4-Chloro-phenyl)-2,3-dimethyl-isoxazolidin-3-yl]-pyridine (Pyrisoxazole) |
| D-119 | one individualized compound I | 3-[5-(4-Methyl-phenyl)-2,3-dimethyl-isoxazolidin-3-yl]-pyridine |
| D-120 | one individualized compound I | Bupirimate |
| D-121 | one individualized compound I | Cyprodinil |
| D-122 | one individualized compound I | 5-Fluorocytosine |

TABLE D-continued

Composition comprising one indiviualized compound I
and one further active substance from groups A) to O)

| Mixture | Component 1 | Component 2 |
| --- | --- | --- |
| D-123 | one individualized compound I | 5-Fluoro-2-(p-tolylmethoxy)pyrimidin-4-amine |
| D-124 | one individualized compound I | 5-Fluoro-2-(4-fluorophenylmethoxy)-pyrimidin-4-amine |
| D-125 | one individualized compound I | Diflumetorim |
| D-126 | one individualized compound I | (5,8-Difluoroquinazolin-4-yl)-{2-[2-fluoro-4-(4-trifluoromethylpyridin-2-yloxy)-phenyl]-ethyl}-amine |
| D-127 | one individualized compound I | Fenarimol |
| D-128 | one individualized compound I | Ferimzone |
| D-129 | one individualized compound I | Mepanipyrim |
| D-130 | one individualized compound I | Nitrapyrin |
| D-131 | one individualized compound I | Nuarimol |
| D-132 | one individualized compound I | Pyrimethanil |
| D-133 | one individualized compound I | Triforine |
| D-134 | one individualized compound I | Fenpiclonil |
| D-135 | one individualized compound I | Fludioxonil |
| D-136 | one individualized compound I | Aldimorph |
| D-137 | one individualized compound I | Dodemorph |
| D-138 | one individualized compound I | Dodemorph-acetate |
| D-139 | one individualized compound I | Fenpropimorph |
| D-140 | one individualized compound I | Tridemorph |
| D-141 | one individualized compound I | Fenpropidin |
| D-142 | one individualized compound I | Fluoroimid |
| D-143 | one individualized compound I | Iprodione |
| D-144 | one individualized compound I | Procymidone |
| D-145 | one individualized compound I | Vinclozolin |
| D-146 | one individualized compound I | Famoxadone |
| D-147 | one individualized compound I | Fenamidone |
| D-148 | one individualized compound I | Flutianil |
| D-149 | one individualized compound I | Octhilinone |
| D-150 | one individualized compound I | Probenazole |
| D-151 | one individualized compound I | Fenpyrazamine |
| D-152 | one individualized compound I | Acibenzolar-S-methyl |
| D-153 | one individualized compound I | Ametoctradin |
| D-154 | one individualized compound I | Amisulbrom |
| D-155 | one individualized compound I | [(3S,6S,7R,8R)-8-benzyl-3-[(3-iso-butyryloxymethoxy-4-methoxypyridine-2-carbonyl)amino]-6-methyl-4,9-dioxo-[1,5]dioxonan-7-yl] 2-methylpropanoate |
| D-156 | one individualized compound I | [(3S,6S,7R,8R)-8-benzyl-3-[(3-acetoxy-4-methoxy-pyridine-2-carbonyl)amino]-6-methyl-4,9-dioxo-1,5-dioxonan-7-yl] 2-methylpropanoate |
| D-157 | one individualized compound I | [(3S,6S,7R,8R)-8-benzyl-3-[[3-(acetoxymethoxy)-4-methoxy-pyridine-2-carbonyl]amino]-6-methyl-4,9-dioxo-1,5-dioxonan-7-yl] 2-methylpropanoate |
| D-158 | one individualized compound I | [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl] 2-methylpropanoate |
| D-159 | one individualized compound I | [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl] 2-methylpropanoate |
| D-160 | one individualized compound I | (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate |
| D-161 | one individualized compound I | Anilazin |
| D-162 | one individualized compound I | Blasticidin-S |
| D-163 | one individualized compound I | Captafol |
| D-164 | one individualized compound I | Captan |
| D-165 | one individualized compound I | Chinomethionat |
| D-166 | one individualized compound I | Dazomet |
| D-167 | one individualized compound I | Debacarb |
| D-168 | one individualized compound I | Diclomezine |
| D-169 | one individualized compound I | Difenzoquat, |
| D-170 | one individualized compound I | Difenzoquat-methylsulfate |
| D-171 | one individualized compound I | Fenoxanil |
| D-172 | one individualized compound I | Folpet |
| D-173 | one individualized compound I | Oxolinsäure |
| D-174 | one individualized compound I | Piperalin |
| D-175 | one individualized compound I | Proquinazid |

TABLE D-continued

Composition comprising one indiviualized compound I
and one further active substance from groups A) to O)

| Mixture | Component 1 | Component 2 |
| --- | --- | --- |
| D-176 | one individualized compound I | Pyroquilon |
| D-177 | one individualized compound I | Quinoxyfen |
| D-178 | one individualized compound I | Triazoxid |
| D-179 | one individualized compound I | Tricyclazole |
| D-180 | one individualized compound I | 2-Butoxy-6-iodo-3-propyl-chromen-4-one |
| D-181 | one individualized compound I | 5-Chloro-1-(4,6-dimethoxy-pyrimidin-2-yl)-2-methyl-1H-benzoimidazole |
| D-182 | one individualized compound I | 5-Chloro-7-(4-methyl-piperidin-1-yl)-6-(2,4,6-trifluoro-phenyl)-[1,2,4]triazolo[1,5-a]pyrimidine |
| D-183 | one individualized compound I | Ferbam |
| D-184 | one individualized compound I | Mancozeb |
| D-185 | one individualized compound I | Maneb |
| D-186 | one individualized compound I | Metam |
| D-187 | one individualized compound I | Methasulphocarb |
| D-188 | one individualized compound I | Metiram |
| D-189 | one individualized compound I | Propineb |
| D-190 | one individualized compound I | Thiram |
| D-191 | one individualized compound I | Zineb |
| D-192 | one individualized compound I | Ziram |
| D-193 | one individualized compound I | Diethofencarb |
| D-194 | one individualized compound I | Benthiavalicarb |
| D-195 | one individualized compound I | Iprovalicarb |
| D-196 | one individualized compound I | Propamocarb |
| D-197 | one individualized compound I | Propamocarb hydrochlorid |
| D-198 | one individualized compound I | Valifenalate |
| D-199 | one individualized compound I | N-(1-(1-(4-cyanophenyl)ethane-sulfonyl)-but-2-yl) carbamic acid-(4-fluorophenyl) ester |
| D-200 | one individualized compound I | Dodine |
| D-201 | one individualized compound I | Dodine free base |
| D-202 | one individualized compound I | Guazatine |
| D-203 | one individualized compound I | Guazatine-acetate |
| D-204 | one individualized compound I | Iminoctadine |
| D-205 | one individualized compound I | Iminoctadine-triacetate |
| D-206 | one individualized compound I | Iminoctadine-tris(albesilate) |
| D-207 | one individualized compound I | Kasugamycin |
| D-208 | one individualized compound I | Kasugamycin-hydrochloride-hydrate |
| D-209 | one individualized compound I | Polyoxine |
| D-210 | one individualized compound I | Streptomycin |
| D-211 | one individualized compound I | Validamycin A |
| D-212 | one individualized compound I | Binapacryl |
| D-213 | one individualized compound I | Dicloran |
| D-214 | one individualized compound I | Dinobuton |
| D-215 | one individualized compound I | Dinocap |
| D-216 | one individualized compound I | Nitrothal-isopropyl |
| D-217 | one individualized compound I | Tecnazen |
| D-218 | one individualized compound I | Fentin salts |
| D-219 | one individualized compound I | Dithianon |
| D-220 | one individualized compound I | 2,6-dimethyl-1H,5H-[1,4]dithiino[2,3-c:5,6-c']dipyrrole-1,3,5,7(2H,6H)-tetraone |
| D-221 | one individualized compound I | Isoprothiolane |
| D-222 | one individualized compound I | Edifenphos |
| D-223 | one individualized compound I | Fosetyl, Fosetyl-aluminium |
| D-224 | one individualized compound I | Iprobenfos |
| D-225 | one individualized compound I | Phosphorous acid ($H_3PO_3$) and derivatives |
| D-226 | one individualized compound I | Pyrazophos |
| D-227 | one individualized compound I | Tolclofos-methyl |
| D-228 | one individualized compound I | Chlorothalonil |
| D-229 | one individualized compound I | Dichlofluanid |
| D-230 | one individualized compound I | Dichlorophen |
| D-231 | one individualized compound I | Flusulfamide |
| D-232 | one individualized compound I | Hexachlorbenzene |
| D-233 | one individualized compound I | Pencycuron |
| D-234 | one individualized compound I | Pentachlorophenol and salts |
| D-235 | one individualized compound I | Phthalide |
| D-236 | one individualized compound I | Quintozene |
| D-237 | one individualized compound I | Thiophanate Methyl |
| D-238 | one individualized compound I | Tolylfluanid |
| D-239 | one individualized compound I | N-(4-chloro-2-nitro-phenyl)-N-ethyl-4-methyl-benzenesulfonamide |

TABLE D-continued

Composition comprising one indiviualized compound I
and one further active substance from groups A) to O)

| Mixture | Component 1 | Component 2 |
|---|---|---|
| D-240 | one individualized compound I | Bordeaux mixture |
| D-241 | one individualized compound I | Copper acetate |
| D-242 | one individualized compound I | Copper hydroxide |
| D-243 | one individualized compound I | Copper oxychloride |
| D-244 | one individualized compound I | basic Copper sulfate |
| D-245 | one individualized compound I | Sulfur |
| D-246 | one individualized compound I | Biphenyl |
| D-247 | one individualized compound I | Bronopol |
| D-248 | one individualized compound I | Cyflufenamid |
| D-249 | one individualized compound I | Cymoxanil |
| D-250 | one individualized compound I | Diphenylamin |
| D-251 | one individualized compound I | Metrafenone |
| D-252 | one individualized compound I | Pyriofenone |
| D-253 | one individualized compound I | Mildiomycin |
| D-254 | one individualized compound I | Oxin-copper |
| D-255 | one individualized compound I | Oxathiapiprolin |
| D-256 | one individualized compound I | Prohexadione calcium |
| D-257 | one individualized compound I | Spiroxamine |
| D-258 | one individualized compound I | Tebufloquin |
| D-259 | one individualized compound I | Tolylfluanid |
| D-260 | one individualized compound I | N-(Cyclopropylmethoxyimino-(6-difluoromethoxy-2,3-difluoro-phenyl)-methyl)-2-phenyl acetamide |
| D-261 | one individualized compound I | N'-(4-(4-chloro-3-trifluoromethyl-phenoxy)-2,5-dimethyl-phenyl)-N-ethyl-N-methyl formamidine |
| D-262 | one individualized compound I | N'-(4-(4-fluoro-3-trifluoromethyl-phenoxy)-2,5-dimethyl-phenyl)-N-ethyl-N-methyl formamidine |
| D-263 | one individualized compound I | N'-(2-methyl-5-trifluoromethyl-4-(3-tri-methylsilanyl-propoxy)-phenyl)-N-ethyl-N-methyl formamidine |
| D-264 | one individualized compound I | N'-(5-difluoromethyl-2-methyl-4-(3-tri-methylsilanyl-propoxy)-phenyl)-N-ethyl-N-methyl formamidine |
| D-265 | one individualized compound I | Methoxy-acetic acid 6-tert-butyl-8-fluoro-2,3-dimethyl-quinolin-4-yl ester |
| D-266 | one individualized compound I | *Bacillus subtilis* NRRL No. B-21661 |
| D-267 | one individualized compound I | *Bacillus pumilus* NRRL No. B-30087 |
| D-268 | one individualized compound I | *Ulocladium oudemansii* |
| D-269 | one individualized compound I | Carbaryl |
| D-270 | one individualized compound I | Carbofuran |
| D-271 | one individualized compound I | Carbosulfan |
| D-272 | one individualized compound I | Methomylthiodicarb |
| D-273 | one individualized compound I | Bifenthrin |
| D-274 | one individualized compound I | Cyfluthrin |
| D-275 | one individualized compound I | Cypermethrin |
| D-276 | one individualized compound I | alpha-Cypermethrin |
| D-277 | one individualized compound I | zeta-Cypermethrin |
| D-278 | one individualized compound I | Deltamethrin |
| D-279 | one individualized compound I | Esfenvalerate |
| D-280 | one individualized compound I | Lambda-cyhalothrin |
| D-281 | one individualized compound I | Permethrin |
| D-282 | one individualized compound I | Tefluthrin |
| D-283 | one individualized compound I | Diflubenzuron |
| D-284 | one individualized compound I | Flufenoxuron |
| D-285 | one individualized compound I | Lufenuron |
| D-286 | one individualized compound I | Teflubenzuron |
| D-287 | one individualized compound I | Spirotetramate |
| D-288 | one individualized compound I | Clothianidin |
| D-289 | one individualized compound I | Dinotefuran |
| D-290 | one individualized compound I | Imidacloprid |
| D-291 | one individualized compound I | Thiamethoxam |
| D-292 | one individualized compound I | Flupyradifurone |
| D-293 | one individualized compound I | Acetamiprid |
| D-294 | one individualized compound I | Thiacloprid |
| D-295 | one individualized compound I | Endosulfan |
| D-296 | one individualized compound I | Fipronil |
| D-297 | one individualized compound I | Abamectin |
| D-298 | one individualized compound I | Emamectin |
| D-299 | one individualized compound I | Spinosad |
| D-300 | one individualized compound I | Spinetoram |
| D-301 | one individualized compound I | Hydramethylnon |
| D-302 | one individualized compound I | Chlorfenapyr |
| D-303 | one individualized compound I | Fenbutatin oxide |

TABLE D-continued

Composition comprising one indiviualized compound I
and one further active substance from groups A) to O)

| Mixture | Component 1 | Component 2 |
|---|---|---|
| D-304 | one individualized compound I | Indoxacarb |
| D-305 | one individualized compound I | Metaflumizone |
| D-306 | one individualized compound I | Flonicamid |
| D-307 | one individualized compound I | Lubendiamide |
| D-308 | one individualized compound I | Chlorantraniliprole |
| D-309 | one individualized compound I | Cyazypyr (HGW86) |
| D-310 | one individualized compound I | Cyflumetofen |
| D-311 | one individualized compound I | Acetochlor |
| D-312 | one individualized compound I | Dimethenamid |
| D-313 | one individualized compound I | metolachlor |
| D-314 | one individualized compound I | Metazachlor |
| D-315 | one individualized compound I | Glyphosate |
| D-316 | one individualized compound I | Glufosinate |
| D-317 | one individualized compound I | Sulfosate |
| D-318 | one individualized compound I | Clodinafop |
| D-319 | one individualized compound I | Fenoxaprop |
| D-320 | one individualized compound I | Fluazifop |
| D-321 | one individualized compound I | Haloxyfop |
| D-322 | one individualized compound I | Paraquat |
| D-323 | one individualized compound I | Phenmedipham |
| D-324 | one individualized compound I | Clethodim |
| D-325 | one individualized compound I | Cycloxydim |
| D-326 | one individualized compound I | Profoxydim |
| D-327 | one individualized compound I | Sethoxydim |
| D-328 | one individualized compound I | Tepraloxydim |
| D-329 | one individualized compound I | Pendimethalin |
| D-330 | one individualized compound I | Prodiamine |
| D-331 | one individualized compound I | Trifluralin |
| D-332 | one individualized compound I | Acifluorfen |
| D-333 | one individualized compound I | Bromoxynil |
| D-334 | one individualized compound I | Imazamethabenz |
| D-335 | one individualized compound I | Imazamox |
| D-336 | one individualized compound I | Imazapic |
| D-337 | one individualized compound I | Imazapyr |
| D-338 | one individualized compound I | Imazaquin |
| D-339 | one individualized compound I | Imazethapyr |
| D-340 | one individualized compound I | 2,4-Dichlorophenoxyacetic acid (2,4-D) |
| D-341 | one individualized compound I | Chloridazon |
| D-342 | one individualized compound I | Clopyralid |
| D-343 | one individualized compound I | Fluroxypyr |
| D-344 | one individualized compound I | Picloram |
| D-345 | one individualized compound I | Picolinafen |
| D-346 | one individualized compound I | Bensulfuron |
| D-347 | one individualized compound I | Chlorimuron-ethyl |
| D-348 | one individualized compound I | Cyclosulfamuron |
| D-349 | one individualized compound I | Iodosulfuron |
| D-350 | one individualized compound I | Mesosulfuron |
| D-351 | one individualized compound I | Metsulfuron-methyl |
| D-352 | one individualized compound I | Nicosulfuron |
| D-353 | one individualized compound I | Rimsulfuron |
| D-354 | one individualized compound I | Triflusulfuron |
| D-355 | one individualized compound I | Atrazine |
| D-356 | one individualized compound I | Hexazinone |
| D-357 | one individualized compound I | Diuron |
| D-358 | one individualized compound I | Florasulam |
| D-359 | one individualized compound I | Pyroxasulfone |
| D-360 | one individualized compound I | Bentazone |
| D-361 | one individualized compound I | Cinidon-ethyl |
| D-362 | one individualized compound I | Cinmethylin |
| D-363 | one individualized compound I | Dicamba |
| D-364 | one individualized compound I | Diflufenzopyr |
| D-365 | one individualized compound I | Quinclorac |
| D-366 | one individualized compound I | Quinmerac |
| D-367 | one individualized compound I | Mesotrione |
| D-368 | one individualized compound I | Saflufenacil |
| D-369 | one individualized compound I | Topramezone |
| D-370 | one individualized compound I | 1,1'-[(3S,4R,4aR,6S,6aS,12R,12aS, 12bS)-4-[[(2-cyclopropylacetyl)oxy]methyl]-1,3,4,4a,5,6,6a,12,12a,12b-deca-hydro-12-hydroxy-4,6a,12b-trimethyl-11-oxo-9-(3-pyridinyl)-2H,11H-naph-tho[2,1-b]pyrano[3,4-e]pyran-3,6-diyl] cyclopropaneacetic acid ester |

The active substances referred to as component 2, their preparation and their activity against harmful fungi is known (cf.: http://www.alanwood.net/pesticides/); these substances are commercially available. The compounds described by IUPAC nomenclature, their preparation and their fungicidal activity are also known (cf. Can. J. Plant Sci. 48(6), 587-94, 1968; EP-A 141 317; EP-A 152 031; EP-A 226 917; EP-A 243 970; EP-A 256 503; EP-A 428 941; EP-A 532 022; EP-A 1 028 125; EP-A 1 035 122; EP-A 1 201 648; EP-A 1 122 244, JP 2002316902; DE 19650197; DE 10021412; DE 102005009458; U.S. Pat. No. 3,296,272; U.S. Pat. No. 3,325, 503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 11/028,657).

The mixtures of active substances can be prepared as compositions comprising besides the active ingredients at least one inert ingredient by usual means, e.g. by the means given for the compositions of compounds I.

Concerning usual ingredients of such compositions reference is made to the explanations given for the compositions containing compounds I.

The mixtures of active substances according to the present invention are suitable as fungicides, as are the compounds of formula I. They are distinguished by an outstanding effectiveness against a broad spectrum of phytopathogenic fungi, especially from the classes of the Ascomycetes, Basidiomycetes, Deuteromycetes and Peronosporomycetes (syn. Oomycetes). In addition, it is referred to the explanations regarding the fungicidal activity of the compounds and the compositions containing compounds I, respectively.

I. SYNTHESIS EXAMPLES

With appropriate modification of the starting materials, the procedures given in the synthesis examples below were used to obtain further compounds I. The compounds produced in this manner are listed in Table V below including corresponding physical data. 2-(2-Chloro-4-hydroxyphenyl)ethylamine-tert-butylcarbamate was prepared as described in WO 2004026305 A1. 2-(2-Fluoro-4-methoxyphenyl)ethylamine hydrochloride was prepared from 2-fluoro-4-methoxybenzaldehyde as described in US 20110054173 A1. 2-(3-Methoxy-4-hydroxyphenyl)ethylamine-tert-butylcarbamate was prepared according to literature precedents in Bioorganic & Medicinal Chemistry (2011), 19(2), 783-788 and in European Journal of Medicinal Chemistry (2008), 43(6), 1160-1170. 6-Dichloro-5-pyrimidinecarboxylic acid methyl ester was prepared from 4,6-dihydroxypyrimidine as described in Journal of Medicinal Chemistry (2010), 53(13), 5012-5024.

Example 1

Preparation of 2-(2-fluoro-4-hydroxyphenyl)ethylamine-tert-butyl carbamate 2-(2-Fluoro-4-methoxyphenyl)ethylamine hydrochloride (270 g, 1.6 mol) was carefully added portionwise to 48% HBr (1.5 L) and stirred for 4 h at 140° C. The reaction solution was reduced in vacuo, then acetonitrile (1 L) was added to the residue and was evaporated to dryness. The crude product was stirred in diisopropylether and recovered by filtration to afford 222 g (940 mmol, 59%) of desired phenol. The purified phenol was dissolved in dichloromethane (DCM, 1.5 L) to which was added triethylamine (275 mL), tert-butyloxycarbonyl anhydride (215 g, 990 mmol) in a solution of DCM (500 mL), and was stirred for 30 min at room temperature. The reaction solution was washed with water, dried over $Na_2SO_4$ and then concentrated in vacuo. The residue was purified by flash silica column chromatography (4:1 cyclohexane:MTBE) to afford 220 g (860 mmol, 92%) of 2-(2-Fluoro-4-hydroxyphenyl)ethylamine-tert-butyl carbamate.

Example 2

Preparation of 2-[4-[[2-(trifluoromethyl)-4-pyridyl]oxy]phenyl]ethanamine hydrochloride To a solution of N-tert-butyloxy-carbonyl-protected tyramine (130 g, 550 mmol), potassium carbonate (76 g, 550 mmol) and catalytic amounts of potassium iodide in N-methyl-2-pyrrolidone (NMP, 400 mL) that was stirred for 10 minutes at room temperature was added 4-chloro-2-trifluoromethylpyridine (100 g, 550 mmol). The reaction mixture was then heated to 160° C. for 6 h, cooled, poured into water and extracted with methyl tert-butylether (MTBE, 3×). The combined organic layers were washed with succesivly with 3 N NaOH and water, dried over $Na_2SO_4$, and reduced in vacuo. The crude residue was purified by flash silica gel column chromatography to afford a 48% (102 g, 265 mmol) yield of N-tert-butyloxycarbonyl-protected 2-[4-[[2-(trifluoromethyl)-4-pyridyl]oxy]phenyl]ethanamine. To a solution of this material in dioxane (200 mL) was added 4 M HCl in dioxane (250 mL). The solution was left overnight to stir at room temperature, which resulted in precipitation of 2-[4-[[2-(trifluoromethyl)-4-pyridyl]oxy]phenyl]ethanamine. The reaction solution was evaporated and the residue was stirred with pentane and filtered to provide 100% (37 g, 104 mmol) of the desired amine hydrochloride.

Example 3

Preparation of 6-chloro-N-[2-[4-(6-chloro-5-methoxy-pyrimidin-4-yl)oxyphenyl]ethyl]-5-methoxy-pyrimidin-4-amine (V-17)

To a solution of 4-hydroxyphenylethylamine hydrochloride (300 mg) in N,N-dimethyl formamide (DMF, 5 mL) was added diisopropylethylamine (355 mg, 2 equiv.). The solution was stirred for 5 min before the addition of 4,6-dichloro-5-methoxypyrimidine (249 mg, 1 equiv.). The reaction mixture was then stirred for 16 h at room temperature before it was concentrated in vacuo. The residue was dissolved in DMF (10 mL) and was stirred with sodium hydride (66 mg, 2.2 equiv.) for 20 min at room temperature. Another portion of 4,6-dichloro-5-methoxypyrimidine (269 mg, 1.2 equiv.) was introduced into the reaction mixture, which was then left to stir at room temperature for 48 h. The DMF was then removed in vacuo and the product was purified by flash silica column chromatography to afford 178 mg (31% yield) of the product as a white solid.

Example 4

Preparation of 6-chloro-N-[2-[2-fluoro-4-[[4-(trifluoromethyl)-2-pyridyl]oxy]phenyl]ethyl]-5-methoxy-pyrimidin-4-amine (V-3)

To a solution of 2-[2-fluoro-4-[[4-(trifluoromethyl)-2-pyridyl]oxy]phenyl]ethanamine hydrochloride (378 mg, 1 mmol) in N-methyl-2-pyrrolidone (5 mL) was added diisopropylethylamine (0.4 mL, 2.3 mmol). The solution was stirred for 5 min at room temperature at which time 4,6-dichloro-5-methylpyrimidine (150 mg, 0.8 mmol) was added. The reaction mixture was stirred at 80° C. overnight then allowed to cool to room temperature. Water was added and was extracted with MTBE (3×). The combined organic layers were washed with water, dried over $Na_2SO_4$, and concentrated in vacuo. The residue was purified by flash silica column chromatography to provide 330 mg (0.80 mmol, 84%) of the light yellow solid product.

The compounds listed in Table V have been prepared in an analogous manner.

II. BIOLOGICAL EXAMPLES FOR FUNGICIDAL ACTIVITY

The fungicidal action of the compounds I was demonstrated by the following experiments:

A. Glass House Trials

The spray solutions were prepared in several steps: The stock solution were prepared: a mixture of acetone and/or dimethylsulfoxide and the wetting agent/emulsifier Wettol, which is based on ethoxylated alkylphenoles, in a relation (volume) solvent-emulsifier of 99 to 1 was added to 25 mg of the compound to give a total of 5 ml. Water was then added to total volume of 100 ml.

TABLE V

Compounds V-1 to V-49 of formula I.A as defined above and wherein $R^1$ and $R^2$ in each case are hydrogen.

| ex. no | $R^{a2}$ | $R^{a5}$ | $R^{a6}$ | Het | R | X | $(R^b)_n$* | HPLC $R_t$ (min) | m.p. (° C.) |
|---|---|---|---|---|---|---|---|---|---|
| V-1 | H | Cl | Cl | H-1 | H | —$CH_2$— | n = 0 | 3.999 | 89 |
| V-2 | H | H | Cl | H-1 | H | —$CH_2$— | n = 0 | 3.568 | 135 |
| V-3 | H | Me | Cl | H-1 | H | —$CH_2$— | o-F; n = 1 | 1.289 | 121 |
| V-4 | H | OMe | Cl | H-1 | H | —$CH_2$— | o-F; n = 1 | 1.297 | 95 |
| V-5 | H | COOMe | Cl | H-2 | H | —$CH_2$— | n = 0 | 1.316 | |
| V-6 | H | COOMe | Cl | H-2 | H | —$CH_2$— | o-F; n = 1 | 1.326 | 112 |
| V-7 | H | Cl | Cl | H-1 | H | —$CH_2$— | o-F; n = 1 | 1.364 | 97 |
| V-8 | H | Cl | Cl | H-1 | H | —$CH_2$— | m-OMe; n = 1 | 1.35 | |
| V-9 | H | Me | Cl | H-2 | H | —$CH_2$— | o-F; n = 1 | 1.221 | |
| V-10 | H | F | Cl | H-1 | H | —$CH_2$— | o-F; n = 1 | 1.332 | 142 |
| V-11 | H | F | Cl | H-2 | H | —$CH_2$— | o-F; n = 1 | 1.278 | 116 |
| V-12 | H | Br | F | H-1 | H | —$CH_2$— | o-F; n = 1 | 1.361 | |
| V-13 | H | Me | Cl | H-1 | H | —$CH_2$— | m-Cl; n = 1 | 1.317 | 120 |
| V-14 | H | OMe | Cl | H-1 | Me | —$CH_2$— | o-F; n = 1 | 1.373 | |
| V-15 | H | CN | Cl | H-1 | H | —$CH_2$— | n = 0 | 1.34 | 105 |
| V-16 | H | OMe | Cl | H-1 | H | —$CH_2$— | m-OMe; n = 1 | 1.231 | 106 |
| V-17 | H | OMe | Cl | H-28 | H | —$CH_2$— | n = 0 | 1.157 | 123 |
| V-18 | H | OMe | Cl | H-7 | H | —$CH_2$— | n = 0 | 1.11 | 125 |
| V-19 | H | OMe | Cl | H-1 | H | —$CH_2$— | n = 0 | 1.27 | |
| V-20 | H | OMe | Cl | H-2 | H | —$CH_2$— | m-OMe; n = 1 | 1.21 | |
| V-21 | H | OMe | Cl | H-2 | H | —$CH_2$— | n = 0 | 1.22 | |
| V-22 | H | OMe | Cl | H-6 | H | —$CH_2$— | n = 0 | 1.1 | 105 |
| V-23 | H | OMe | Cl | H-1 | H | —$CH(CH_2OH)$— | n = 0 | 1.169 | |
| V-24 | H | Me | Cl | H-1 | H | —$CH(CH_2OH)$— | n = 0 | 1.142 | |
| V-25 | Me | Cl | Cl | H-1 | H | —$CH_2$— | o-F; n = 1 | 1.432 | 108 |
| V-26 | Me | Me | Cl | H-1 | H | —$CH_2$— | o-F; n = 1 | 1.172 | |
| V-27 | H | OMe | Cl | H-1 | Me | —$CH_2$— | o-F, n = 1 | 1.373 | |
| V-28 | H | Me | Cl | H-30 | H | —$CH_2$— | n = 0 | 1.173 | 162 |
| V-29 | H | CN | Cl | H-1 | H | —$CH_2$— | o-F; n = 1 | 1.34 | 184 |
| V-30 | H | Cl | Cl | H-2 | H | —$CH(CH_3)$— | n = 0 | 1.36 | 150 |
| V-31 | H | Br | Cl | H-1 | H | —$CH_2$— | o-F; n = 1 | 1.403 | |
| V-32 | H | COOMe | Cl | H-1 | H | —$CH_2$— | o-F; n = 1 | 1.37 | |
| V-33 | Cl | Cl | Cl | H-1 | H | —$CH_2$— | o-F; n = 1 | 1.468 | |
| V-34 | H | Et | Cl | H-1 | H | —$CH_2$— | m-F; n = 1 | 1.338 | |
| V-35 | H | Et | Cl | H-2 | H | —$CH_2$— | m-F; n = 1 | 1.294 | 130 |
| V-36 | H | Br | Cl | H-2 | H | —$CH_2$— | o-F; n = 1 | 1.354 | 132 |
| V-37 | H | Me | Cl | H-1 | H | —$CH_2$— | m-Me; n = 1 | 1.278 | 130 |
| V-38 | Me | Me | Cl | H-2 | H | —$CH_2$— | o-F; n = 1 | 1.140 | 141 |
| V-39 | Me | $C(CH_3)_3$ | Cl | H-1 | H | —$CH_2$— | o-F; n = 1 | 1.238 | |
| V-40 | Me | $C(CH_3)_3$ | Cl | H-2 | H | —$CH_2$— | o-F; n = 1 | 1.199 | |
| V-41 | H | Et | Cl | 6-chloro-5-ethyl-pyrimidin-4-yl | H | —$CH_2$— | n = 0 | 1.291 | 116 |
| V-42 | $NH_2$ | H | Cl | H-1 | H | —$CH_2$— | o-F; n = 1 | 1.052 | |
| V-43 | Me | H | Cl | H-1 | H | —$CH_2$— | o-F; n = 1 | 1.208 | |
| V-44 | H | Me | Cl | H-1 | H | —$CH_2$— | m-F; n = 1 | 1.252 | 126 |
| V-45 | H | Me | Cl | H-7 | H | —$CH_2$— | n = 0 | 1.09 | 139 |
| V-46 | H | Me | Cl | H-8 | H | —$CH_2$— | n = 0 | 1.07 | |
| V-47 | H | Cl | Cl | H-1 | H | —$CH(CH_2OH)$— | n = 0 | 1.228 | |
| V-48 | H | OMe | Cl | H-1 | H | —$CH(COOMe)$— | n = 0 | 1.310 | |
| V-49 | H | Me | Cl | H-1 | H | —$CH(CH_2OCH_3)$— | n = 0 | 1.293 | 87 |

*The position of $R^b$ on the phenyl ring is defined relative to the $CR^1R^2$-moiety bound to the phenyl ring as being in ortho (o-) or meta (m-) position. n = 0 indicates that no substituent $R^b$ is present on the phenyl ring. m.p. = melting point (° C.).
HPLC-MS: HPLC-column Kinetex XB C18 1.7μ (50 × 2.1 mm); eluent: acetonitrile/water + 0.1% TFA (gradient from 5:95 to 100:0 in 1.5 min at 60° C., flow gradient from 0.8 to 1.0 ml/min in 1.5 min). MS: Quadrupol Electrospray Ionisation, 80 V (positive mode).

This stock solution was diluted with the described solvent-emulsifier-water mixture to the given concentration.

After the final cultivation period, the extent of fungal attack on the leaves was visually assessed as % diseased leaf area.

Use Example 1

Protective Control of Soy Bean Rust on Soy Beans Caused by *Phakopsora Pachyrhizi*

Leaves of pot-grown soybean seedlings were sprayed to run-off with an aqueous suspension, containing the concentration of active ingredient or their mixture as described below. The plants were allowed to air-dry. The trial plants were cultivated for 1 day in a greenhouse chamber at 23 to 27° C. and a relative humidity between 60 and 80%. Then the plants were inoculated with spores of *Phakopsora pachyrhizi*. To ensure the success the artificial inoculation, the plants were transferred to a humid chamber with a relative humidity of about 95% and 20-24° C. for 24 h. The trial plants were cultivated for fourteen days in a greenhouse chamber at 23 to 27° C. and a relative humidity between 60 and 80%.

In this test, the plants which had been treated with 250 ppm of the active compound V-1, V-2, V-3, V-4, V-5, V-8, V-10, V-11, V-14, V-16, V-17, V-23, V-26, V-27, V-31, V-32, V-34, V-37, V-42, V-43, V-44, V-47 or V-48 showed a diseased leaf area of at most 20%, whereas the untreated plants showed 94% diseased leaf area.

Use Example 2

Preventative Control of Brown Rust on Wheat Caused by *Puccinia* Recondite

The first two developed leaves of pot-grown wheat seedling were sprayed to run-off with an aqueous suspension, containing the concentration of active ingredient or their mixture as described below. The next day the plants were inoculated with spores of *Puccinia recondita*. To ensure the success the artificial inoculation, the plants were transferred to a humid chamber without light and a relative humidity of 95 to 99% and 20 to 24° C. for 24 h. Then the trial plants were cultivated for 6 days in a greenhouse chamber at 20 to 24° C. and a relative humidity between 65 and 70%.

In this test, the plants which had been treated with 250 ppm of the active compound V-1, V-2, V-4, V-5, V-7, V-10, V-11, V-14, V-15, V-25, V-26, V-27, V-35 or V-38 showed a diseased leaf area of at most 20%, whereas the untreated plants showed 86% diseased leaf area.

Use Example 3

Preventative Control of Leaf Blotch on Wheat Caused by *Septoria tritici*

Leaves of pot-grown wheat seedling were sprayed to run-off with an aqueous suspension of the active compound or their mixture, prepared as described. The plants were allowed to air-dry. At the following day the plants were inoculated with an aqueous spore suspension of *Septoria tritici*. Then the trial plants were immediately transferred to a humid chamber at 18 to 22° C. and a relative humidity close to 100%. After 4 days the plants were transferred to a chamber with 18 to 22° C. and a relative humidity close to 70% and kept there for 4 weeks.

In this test, the plants which had been treated with 250 ppm of the active compound V-1, V-2, V-3, V-4, V-5, V-6, V-7, V-9, V-11, V-12, V-13, V-14, V-15, V-16, V-26, V-27, V-29, V-30, V-31, V-32, V-33, V-36, V-37, V-39 or V-40 showed a diseased leaf area of at most 20%, whereas the untreated plants showed 93% diseased leaf area.

Use Example 4

Control of Late Blight on Tomatoes Caused by *Phytophthora infestans*

Young seedlings of tomato plants were grown in pots. These plants were sprayed to run-off with an aqueous suspension, containing the concentration of active ingredient or their mixture mentioned in the table below. The next day the treated plants were inoculated with an aqueous suspension of sporangia of *Phytophthora infestans*. After inoculation, the trial plants were immediately transferred to a humid chamber and kept for 6 days at 18 to 20° C. and a relative humidity close to 100%.

In this test, the plants which had been treated with 250 ppm of the active compound V-3, V-4, V-6, V-9, V-14, V-15, V-16, V-17, V-18, V-19, V-20, V-21, V-22, V-23, V-24, V-26, V-27, V-28, V-29, V-46 or V-47 showed a diseased leaf area of at most 20%, whereas the untreated plants showed 80% diseased leaf area.

Use Example 5

Control of Late Blight on Tomatoes Caused by *Phytophthora infestans*

Young seedlings of tomato plants were grown in pots. These plants were sprayed to run-off with an aqueous suspension, containing the concentration of active ingredient or their mixture mentioned in the table below. Seven days later the treated plants were inoculated with an aqueous suspension of sporangia of *Phytophthora infestans*. After inoculation, the trial plants were immediately transferred to a humid chamber and kept for 6 days at 18 to 20° C. and a relative humidity close to 100%.

In this test, the plants which had been treated with 250 ppm of the active compound V-4, V-15, V-17, V-23, V-28, V-41, V-45 or V-49 showed a diseased leaf area of at most 20%, whereas the untreated plants showed 60% diseased leaf area.

Use Example 6

Preventative Fungicidal Control of *Botiytis Cinerea* on Leaves of Green Pepper

Young seedlings of green pepper were grown in pots to the 4 to 5 leaf stage. These plants were sprayed to run-off with an aqueous suspension, containing the concentration of active ingredient or their mixture mentioned in the table below. The next day the plants were inoculated with a aqueous biomalt solution containing the spore suspension of *Botrytis cinerea*. Then the plants were immediately transferred to a humid chamber and kept for 5 days at 22 to 24° C. and a relative humidity close to 100%.

In this test, the plants which had been treated with 250 ppm of the active compound V-2, V-4, V-12, V-13, V-15 or V-40 showed a diseased leaf area of at most 20%, whereas the untreated plants showed 89% diseased leaf area.

We claim:
1. A compound of formula I

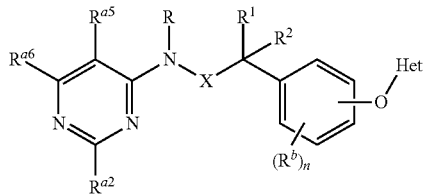

wherein:
$R^{a2}$, $R^{a5}$ independently of each other, are hydrogen, halogen, CN, $NO_2$, OH, SH, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_1$-$C_4$-alkoxy-$C_1$-$C_4$-alkyl, $C_1$-$C_4$-alkoxy-$C_1$-$C_4$-alkoxy, $C_2$-$C_4$-alkenyl, $C_2$-$C_4$-alkynyl, $C_2$-$C_4$-haloalkenyl, $C_2$-$C_4$-haloalkynyl, $C_3$-$C_8$-cycloalkyl, $C_3$-$C_8$-cycloalkyloxy, $C_3$-$C_8$-cycloalkyl-$C_1$-$C_4$-alkyl, $NR^AR^B$, C(=O)R', C(=NOR")R''' or —C(=NH)—O—R''';
$R^A$, $R^B$ independently of each other are hydrogen, $C_1$-$C_4$-alkyl, $C_2$-$C_4$-alkenyl, $C_2$-$C_4$-alkynyl, phenyl, benzyl, $C_3$-$C_8$-cycloalkyl, $C_3$-$C_8$-cycloalkenyl or —C(=O)—R';
R' is hydrogen, OH, $NH_2$, $C_1$-$C_4$-alkyl, $C_1$-$C_4$-haloalkyl, $C_2$-$C_4$-alkenyl, $C_2$-$C_4$-alkynyl, $C_1$-$C_4$-alkoxy, $C_1$-$C_4$-haloalkoxy, $C_1$-$C_4$-alkylamino or di($C_1$-$C_4$-alkyl)amino;
R" is hydrogen, $C_1$-$C_4$-alkyl, $C_1$-$C_4$-haloalkyl, $C_2$-$C_4$-alkenyl, $C_2$-$C_4$-alkynyl or $C_1$-$C_4$-alkoxy-$C_1$-$C_4$-alkyl;
R''' is hydrogen or $C_1$-$C_4$-alkyl;
$R^{a6}$ is halogen;
R is hydrogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkoxy-$C_1$-$C_4$-alkyl, $C_1$-$C_4$-haloalkoxy-$C_1$-$C_4$-alkyl, $C_2$-$C_4$-alkenyl, $C_2$-$C_4$-haloalkenyl, $C_2$-$C_4$-alkynyl, $C_2$-$C_4$-haloalkynyl, CN, $CH_2CN$, $NR^AR^B$ or $CH_2$—O—C(=O)R';
$R^1$, $R^2$ independently of each other are hydrogen, halogen, CN, OH, $C_1$-$C_4$-alkyl, $C_1$-$C_4$-haloalkyl, $C_1$-$C_4$-alkoxy, $C_1$-$C_4$-haloalkoxy, $C_1$-$C_4$-alkoxy-$C_1$-$C_4$-alkyl, $C_1$-$C_4$-haloalkoxy-$C_1$-$C_4$-alkyl, $C_2$-$C_4$-alkenyl, $C_2$-$C_4$-haloalkenyl, $C_2$-$C_4$-alkynyl, $C_2$-$C_4$-haloalkynyl, $C_3$-$C_8$-cycloalkyl, $C_3$-$C_8$-cycloalkyl-$C_1$-$C_4$-alkyl, $C_3$-$C_8$-cycloalkyloxy, $NR^AR^B$, C(=O)R', C(=NOR")R''', —C(=NH)—O—R''' or benzyl wherein the phenyl moiety of benzyl is unsubstituted or carries 1, 2, 3, 4, or 5 substituents selected from the group consisting of CN, halogen, $C_1$-$C_4$-alkyl, $C_1$-$C_4$-haloalkyl, $C_1$-$C_4$-alkoxy, $C_1$-$C_4$-haloalkoxy, ($C_1$-$C_4$-alkoxy)carbonyl and di($C_1$-$C_4$-alkyl)aminocarbonyl, or
two radicals $R^1$ and $R^2$ that are bound to the same carbon atom form together with said carbon atom a saturated or partially unsaturated 3-, 4-, 5-, 6-, or 7-membered carbocycle or a saturated or partially unsaturated 3-, 4-, 5-, 6-, or 7-membered heterocycle, wherein the ring member atoms of the abovementioned heterocycle include beside carbon atoms 1, 2, 3 or 4 heteroatoms selected from the group of N, O and S, and wherein the abovementioned cycle is unsubstituted or carries 1, 2, 3 or 4 substituents selected from halogen, CN, OH, SH, $C_1$-$C_4$-alkyl, $C_1$-$C_4$-alkoxy or $C_1$-$C_4$-alkylthio; and one or two $CH_2$ groups of the abovementioned cycles may be respectively replaced by one or two C=O or C=S groups;
X is a divalent group selected from —$CR^3R^4$—, —C(=$NR^D$)— and —C(=$NOR^D$)—, wherein
$R^D$ is hydrogen or $C_1$-$C_4$-alkyl, and wherein
$R^3$ and $R^4$ independently of each other are hydrogen, CN, $C_1$-$C_4$-hydroxyalkyl, $C_1$-$C_4$-alkyl, $C_1$-$C_4$-haloalkyl, $C_1$-$C_4$-alkoxy, $C_1$-$C_4$-haloalkoxy, $C_1$-$C_4$-alkoxy-$C_1$-$C_4$-alkyl, $C_1$-$C_4$-haloalkoxy-$C_1$-$C_4$-alkyl, $C_2$-$C_4$-alkenyl, $C_2$-$C_4$-haloalkenyl, $C_2$-$C_4$-alkynyl, $C_2$-$C_4$-haloalkynyl, $C_3$-$C_8$-cycloalkyl, $C_3$-$C_8$-cycloalkyl-$C_1$-$C_4$-alkyl, $C_3$-$C_8$-cycloalkyloxy, $NR^AR^B$, C(=O)R', C(=NOR")R''', —C(=NH)—O—R''' or benzyl wherein the phenyl moiety of benzyl is unsubstituted or carries 1, 2, 3, 4, or 5 substituents selected from the group consisting of CN, halogen, $C_1$-$C_4$-alkyl, $C_1$-$C_4$-haloalkyl, $C_1$-$C_4$-alkoxy, $C_1$-$C_4$-haloalkoxy, ($C_1$-$C_4$-alkoxy)carbonyl and di($C_1$-$C_4$-alkyl)aminocarbonyl, or
two radicals $R^3$ and $R^4$ that are bound to the same carbon atom form together with said carbon atom a saturated or partially unsaturated 3-, 4-, 5-, 6-, or 7-membered carbocycle or a saturated or partially unsaturated 3-, 4-, 5-, 6-, or 7-membered heterocycle, wherein the ring member atoms of the abovementioned heterocycle include beside carbon atoms 1, 2, 3 or 4 heteroatoms selected from the group of N, O and S, and wherein the abovementioned cycle is unsubstituted or carries 1, 2, 3 or 4 substituents selected from halogen, CN, OH, SH, $C_1$-$C_4$-alkyl, $C_1$-$C_4$-alkoxy or $C_1$-$C_4$-alkylthio; and one or two $CH_2$ groups of the abovementioned cycles may be respectively replaced by one or two C(=O) or C(=S) groups;
n indicates the number of substituents $R^b$ on the phenyl ring and n is 0, 1, 2, 3 or 4;
$R^b$ is halogen, CN, $NO_2$, $C_1$-$C_4$-alkyl, $C_1$-$C_4$-haloalkyl, $C_1$-$C_4$-alkoxy, $C_1$-$C_4$-haloalkoxy, $C_2$-$C_4$-alkenyl, $C_2$-$C_4$-haloalkenyl, $C_2$-$C_4$-alkynyl, $C_2$-$C_4$-haloalkynyl, $NR^AR^B$, C(=NOR")R''' or —C(=NH)—O—R''',
it being possible for n=2, 3 or 4 that $R^b$ are identical or different;
Het is a 5- or 6-membered heteroaryl, wherein the ring member atoms of the heteroaryl include besides carbon atoms 1, 2, 3 or 4 heteroatoms selected from the group of N, O and S and wherein the heteroaryl is unsubstituted or carries 1, 2, 3 or 4 identical or different groups $R^c$:
$R^c$ is halogen, CN, $NO_2$, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylamino, di($C_1$-$C_6$-alkyl)amino, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_1$-$C_6$-alkoxy-$C_1$-$C_4$-alkyl, $C_1$-$C_6$-haloalkoxy-$C_1$-$C_4$-alkyl, $C_2$-$C_6$-alkenyl, $C_2$-$C_6$-alkynyl, C(=O)R', C(=NOR")R''', $C_3$-$C_8$-cycloalkyl, $C_3$-$C_8$-cycloalkyl-$C_1$-$C_4$-alkyl, phenyl, phenoxy, phenoxy-$C_1$-$C_4$-alkyl or a 5- or 6-membered heteroaryl, wherein the ring member atoms of the heteroaryl include besides carbon atoms 1, 2, 3 or 4 heteroatoms selected from the group of N, O and S, and wherein the aforementioned cyclic radicals are unsubstituted or carry 1, 2, 3 or 4 identical or different substituents $R^d$:
$R^d$ is halogen, CN, $C_1$-$C_4$-haloalkyl, $C_1$-$C_4$-alkoxy or $C_1$-$C_4$-haloalkoxy;

or two radicals $R^c$ that are bound to adjacent ring member atoms of the Het group form together with said ring member atoms a fused 5-, 6- or 7-membered saturated, partially unsaturated or aromatic carbocycle or heterocycle, wherein the ring member atoms of the fused heterocycle include besides carbon atoms 1, 2, 3 or 4 heteroatoms selected from the group of N, O and S, and wherein the fused carbocycle or heterocycle is unsubstituted or carries 1, 2, 3 or 4 identical or different radicals groups $R^e$:

$R^e$ is halogen, CN, $C_1$-$C_4$-haloalkyl, $C_1$-$C_4$-alkoxy or $C_1$-$C_4$-haloalkoxy;

and the N-oxides and the agriculturally acceptable salts of the compounds of formula I.

2. The compound according to claim 1, wherein $R^{a2}$ and $R^{a5}$ independently of each other are halogen, CN, $C_1$-$C_4$-alkyl, $C_1$-$C_4$-alkoxy, haloalkoxy, $C_1$-$C_4$-alkoxy-$C_1$-$C_4$-alkyl, $C_1$-$C_4$-alkoxy-$C_1$-$C_4$-alkoxy or ($C_1$-$C_4$-alkoxy)-carbonyl, and it being possible that one of both, $R^{a2}$ or $R^{a5}$ can in addition be hydrogen.

3. The compound according to claim 1, wherein $R^{a6}$ is chlorine or fluorine.

4. The compound according to claim 1, wherein X is —$CH_2$—.

5. The compound according to claim 1, wherein $R^1$ and $R^2$ are both hydrogen.

6. The compound according to claim 1, wherein Het is selected from the group consisting of pyrimidin-2-yl, pyrimidin-3-yl, pyrimidin-4-yl, pyridin-2-yl, pyridin-3-yl, thiazol-2-yl, pyrazin-2-yl, pyridazin-3-yl, 1,3,5-triazin-2-yl, and 1,2,4-triazin-3-yl.

7. The compound according to claim 1, wherein Het carries 1 or 2 radicals $R^c$ which are selected from F, Cl, Br, CN, $C_1$-$C_2$-alkylsulfonyl, $C_1$-$C_2$-alkoxycarbonyl, aminocarbonyl, $C_1$-$C_2$-alkylaminocarbonyl, di($C_1$-$C_2$-alkyl)aminocarbonyl, $C_1$-$C_2$-alkoxy, $CF_3$, $CHF_2$, $OCF_3$ and $OCHF_2$.

8. The compound according to claim 1, wherein R is hydrogen.

9. A process for preparing the compound of claim 1, wherein X is —$CR^3R^4$—, which comprises reacting a compound of formula II

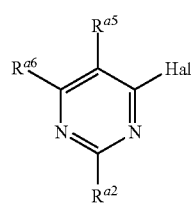

wherein $R^{a2}$, $R^{a5}$ and $R^{a6}$ are as defined in claim 1, Hal is fluorine, chlorine or bromine, with a compound of formula III

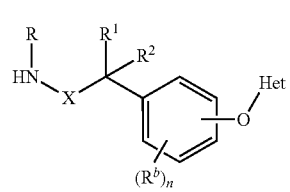

wherein R, $R^1$, $R^2$, $R^b$, n and Het are as defined in claim 1 and X is —$CR^3R^4$— as defined in claim 1 in the presence of a base or a catalyst or a combination of a base and a catalyst in a solvent.

10. An agrochemical composition which comprises an auxiliary and at least one compound of claim 1.

11. The agrochemical composition according to claim 10 comprising at least one further active substance.

12. A method for combating phytopathogenic harmful fungi, which method comprises treating the fungi or the materials, plants, the soil or seeds to be protected against fungal attack, with an effective amount of at least one compound of claim 1.

13. The method of claim 12, wherein, in the compound of formula I, $R^{a2}$ and $R^{a5}$ independently of each other are halogen, CN, $C_1$-$C_4$-alkyl, $C_1$-$C_4$-haloalkyl, $C_1$-$C_4$-alkoxy, $C_1$-$C_4$-haloalkoxy, $C_1$-$C_4$-alkoxy-$C_1$-$C_4$-alkyl, $C_1$-$C_4$-alkoxy-$C_1$-$C_4$-alkoxy or ($C_1$-$C_4$-alkoxy)-carbonyl, and it being possible that one of both, $R^{a2}$ or $R^{a5}$ can in addition be hydrogen.

14. The method of claim 12, wherein, in the compound of formula I, $R^{a6}$ is chlorine or fluorine.

15. The method of claim 12, wherein, in the compound of formula I, X is —$CH_2$—.

16. The method of claim 12, wherein, in the compound of formula I, $R^1$ and $R^2$ are both hydrogen.

17. The method of claim 12, wherein, in the compound of formula I, Het is selected from the group consisting of pyrimidin-2-yl, pyrimidin-3-yl, pyrimidin-4-yl, pyridine-2-yl, pyridin-3-yl, thiazol-2-yl, pyrazin-2-yl, pyridazin-3-yl, 1,3,5-triazin-2-yl, and 1,2,4-triazin-3-yl.

18. The method of claim 12, wherein, in the compound of formula I, Het carries 1 or 2 radicals $R^c$ which are selected from F, Cl, Br, CN, $C_1$-$C_2$-alkylsulfonyl, $C_1$-$C_2$-alkoxycarbonyl, aminocarbonyl, $C_1$-$C_2$-alkylaminocarbonyl, di($C_1$-$C_2$-alkyl)aminocarbonyl, $C_1$-$C_2$-alkoxy, $CF_3$, $CHF_2$, $OCF_3$ and $OCHF_2$.

19. The method of claim 12, wherein, in the compound of formula I, R is hydrogen.

* * * * *